United States Patent [19]

Krüger et al.

[11] Patent Number: 4,575,516
[45] Date of Patent: Mar. 11, 1986

[54] CYCLOPROPYLMETHYL(ENE) ETHERS AND ARTHROPOCIDAL USE THEREOF

[75] Inventors: Bernd-Wieland Krüger, Wuppertal; Uwe Priesnitz, Solingen; Gerhard Jäger, Leverkusen; Wolfgang Behrenz, Overath, all of Fed. Rep. of Germany

[73] Assignee: Bayer Aktiengesellschaft, Leverkusen, Fed. Rep. of Germany

[21] Appl. No.: 576,073

[22] Filed: Feb. 1, 1984

[30] Foreign Application Priority Data

Feb. 19, 1983 [DE] Fed. Rep. of Germany ....... 3305835

[51] Int. Cl.⁴ .................. C07C 43/15; C07C 43/162; C07C 43/166; A01N 43/00
[52] U.S. Cl. .................. 514/715; 568/669; 568/661; 568/39; 564/454; 564/455; 514/717; 514/719; 514/713; 514/659
[58] Field of Search ............... 568/669, 661; 560/124; 514/715

[56] References Cited

PUBLICATIONS

Elliot et al., Chemical Society Reviews, vol. 7, No. 4 (1978) 473–485.

*Primary Examiner*—Bernard Helfin
*Attorney, Agent, or Firm*—Sprung Horn Kramer & Woods

[57] ABSTRACT

Substituted cyclopropylmethyl(ene) ethers of the formula

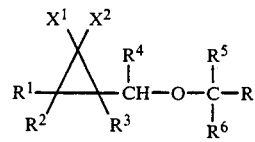

in which $X^1$ and $X^2$ are identical or different and represent halogen, $R^1$ represents hydrogen or alkyl, $R^2$ and $R^3$ are identical or different and represent hydrogen, alkyl, optionally substituted aryl, halogenoalkyl, hetero-alkyl, alkoxyalkyl, alkylthioalkyl, optionally substituted alkenoxyalkyl, optionally substituted alkinoxyalkyl or (di)alkylaminoalkyl, $R^4$ represents hydrogen or alkyl, $R^5$ and $R^6$ are identical or different and represent hydrogen or optionally substituted radicals from the series comprising alkyl, aryl and aralkyl and R represents a trihalogenoalkenyl, alkinyl or iodoalkinyl radical, exhibit some arthropodicidal activity and synergize other known arthropodicides.

17 Claims, No Drawings

CYCLOPROPYLMETHYL(ENE) ETHERS AND ARTHROPOCIDAL USE THEREOF

The present invention relates to new substituted cyclopropylmethyl(ene) ethers, several processes for their preparation and their use as agents for combating pests, preferably for combating arthropods, in particular insects, ticks and arachnids.

Synergistic mixtures of insecticidal active compounds, for example of pyrethroids with certain methylenedioxyphenyl derivatives, for example piperonylbutoxide, as synergists have already been disclosed (compare, for example, K. Naumann, Chemie der Pflanzenschutz- und Schädlingsbekampfungsmittel (Chemistry of Plant Protection Agents and Agents for Combating Pests), SpringerVerlag Berlin, volume 7 (1981), pages 3 to 6). However, in practice, the effectiveness of such products is not always completely satisfactory.

New substituted cyclopropylmethyl(ene) ethers of the general formula (I)

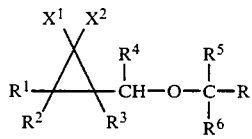

in which
X$^1$ and X$^2$ are identical or different and represent halogen,
R$^1$ represents hydrogen or alkyl,
R$^2$ and R$^3$ are identical or different and represent hydrogen, alkyl, optionally substituted aryl, halogenoalkyl, hetero-alkyl, alkoxyalkyl, alkylthioalkyl, optionally substituted alkenoxyalkyl, optionally substituted alkinoxyalkyl or (di)alkylaminoalkyl,
R$^4$ represents hydrogen or alkyl,
R$^5$ and R$^6$ are identical or different and represent hydrogen or optionally substituted radicals from the series comprising alkyl, aryl and aralkyl and
R represents a trihalogenoalkenyl, alkinyl or iodoalkinyl radical, which can be used as synergists in pest-combating agents additionally containing substances which are active against arthropods, preferably against insects and arachnids, especially against insects, have been found.

Virtually all the customary active compounds can be used as substances which are active against arthropods (compare, for example, K. H. Buchel, Pflanzenschutz- und Schadlingsbekampfungsmittel (Plant Protection Agents and Agents for Combating Pests), Thieme-Verlag Stuttgart, 1977, and Farm Chemicals Handbook, 1979, Meister Publishing Co, Willoughby, 1979).

It has furthermore been found that the new substituted cyclopropylmethyl(ene) ethers of the formula (I) are obtained by a process in which (a) cyclopropylmethyl(ene) halides of the general formula (II)

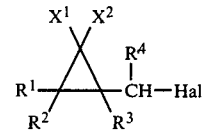

in which
R$^1$, R$^2$, R$^3$, R$^4$, X$^1$ and X$^2$ have the abovementioned meaning and
Hal represents halogen, such as, in particular, chlorine, bromine or iodine, are reacted with alcohols of the general formula (III)

in which
R$^5$ and R$^6$ have the abovementioned meaning and
R' represents alkinyl, or salts thereof, if appropriate in the presence of acid acceptors and/or if appropriate in the presence of diluents, or (b) the new compounds, prepared according to process variant (a), of the general formula (Ia)

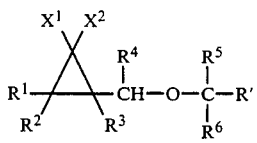

in which
R$^1$, R$^2$, R$^3$, R$^4$, R$^5$, R$^6$, X$^1$ and X$^2$ have the abovementioned meanings, are reacted with equimolar or excess iodine in the presence of acid acceptors and, if appropriate, in the presence of a diluent, or (c) the new compounds, prepared according to process (b), of the general formula (Ib)

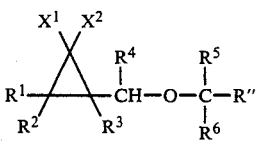

in which
R$^1$, R$^2$, R$^3$, R$^4$, R$^5$, R$^6$, X$^1$ and X$^2$ have the abovementioned meanings and
R" represents iodoalkinyl, are reacted with halogen, such as chlorine, bromine or iodine, if appropriate in the presence of a diluent.

Alkyl R$^1$, R$^2$, R$^3$ and R$^4$ and optionally substituted alkyl R$^5$ and R$^6$ represent straight-chain or branched alkyl with 1 to 20, preferably 1 to 10, in particular 1 to 6 and particularly preferably 1 to 4, carbon atoms. Examples which may be mentioned are optionally substituted methyl, ethyl, n- and iso-propyl and n-, iso-, sec.- and tert.- butyl.

Iodoalkinyl R and R" and alkinyl R and R' preferably contain 2 to 5, in particular 2 to 4, carbon atoms in the alkinyl part. Examples which may be mentioned are ethinyl, propin-1-yl, propin-2-yl and butin-3-yl and the corresponding iodine derivatives.

Optionally substituted aryl $R^2$, $R^3$, $R^5$ and $R^6$ represent aryl with preferably 6 to 10 carbon atoms in the aryl part. Examples which may be mentioned are optionally substituted phenyl or naphthyl, in particular phenyl.

Optionally substituted aralkyl $R^5$ and $R^6$ represents aralkyl which is optionally substituted in the aryl part and/or alkyl part and has preferably 6 to 10, in particular 6, carbon atoms in the aryl part and preferably 1 to 4, in particular 1 or 2, carbon atoms in the alkyl part, it being possible for the alkyl part to be straight-chain or branched. Examples which may be mentioned are optionally substituted benzyl and phenethyl.

Halogenoalkyl radicals $R^2$ and $R^3$ contain preferably 1 to 4 carbon atoms, in particular 1 or 2 carbon atoms, in the alkyl part and preferably 1 to 5, in particular 1 to 3, halogen atoms, the halogen atoms being identical or different, and halogen atoms preferably being chlorine or bromine. Examples which may be mentioned are chloromethyl and bromomethyl.

Alkoxyalkyl and alkylthioalkyl $R^2$ and $R^3$ contain preferably 1 to 4 carbon atoms, in particular 1 or 2 carbon atoms, per alkyl part, it being possible for the alkyl part to be straight-chain or branched. Examples which may be mentioned are methoxymethyl, ethoxymethyl, methoxyethyl, ethoxyethyl, methylthioethyl, ethylthiomethyl and ethylthioethyl.

Optionally substituted alkenoxyalkyl $R^2$ and $R^3$ represents alkenoxyalkyl which is optionally substituted in the alkenoxy part and/or alkyl part and has preferably 2 to 5, in particular 2 to 4, carbon atoms in the alkenoxy part and preferably 1 to 4, in particular 1 or 2, carbon atoms in the alkyl part, it being possible for the alkyl part to be straight-chain or branched. Examples which may be mentioned are optionally substituted propenyloxymethyl, butenyloxymethyl and methylpropenyloxymethyl.

Optionally substituted alkinoxyalkyl $R^2$ and $R^3$ represents alkinoxyalkyl which is optionally substituted in the alkinoxy part and/or alkyl part and has preferably 2 to 5, in particular 2 to 4, carbon atoms in the alkinoxy part and preferably 1 to 4, in particular 1 or 2, carbon atoms in the alkyl part, it being possible for the alkyl part to be straight-chain or branched. Examples which may be mentioned are optionally substituted propinyloxymethyl, butinyloxymethyl and methylpropinyloxymethyl.

(Di)alkylamino-alkyl $R^2$ and $R^3$ contain preferably 1 to 4 carbon atoms, in particular 1 or 2 carbon atoms, in the alkyl part. Examples which may be mentioned are (di)methylamino-methyl, (di)methylamino-ethyl, (di)ethylamino-methyl and (di)ethylamino-ethyl. (Di)alkylamino-alkyl denotes mono- or di-alkylamino-alkyl.

Hetero-alkyl radicals $R^2$ and $R^3$ contain, in the hetaryl part, 5-membered to 7-membered, preferably 5-membered or 6-membered, rings with preferably 1 to 3, in particular 1 or 2, identical or different hetero-atoms, such as O, S and/or N, preferably nitrogen, and, in the alkyl part, 1 to 4 carbon atoms, in particular 1 or 2 carbon atoms. Examples which may be mentioned are 1-pyrazolylmethyl, 1-imidazolylmethyl and 1-(1,2,4-triazolyl)-methyl.

Halogen (or halogen atom) denotes fluorine, chlorine, bromine or iodine, preferably (unless indicated otherwise) fluorine, chlorine or bromine, and particularly preferably chlorine or bromine.

Trihalogenoalkenyl R contains, in the alkenyl part, straight-chain or branched alkenyl with preferably 2 to 5, in particular 2 to 4, carbon atoms. The halogen atoms can be identical or different and preferably represent fluorine, chlorine, bromine and/or iodine, in particular chlorine, bromine and/or iodine. Examples which may be mentioned are triiodoethenyl, dibromo-iodoethenyl and dichloro-iodoethenyl.

The substituted radicals mentioned in the definition of $R^2$, $R^3$, $R^5$ and $R^6$ can carry one or more, preferably 1 to 3 and in particular 1 or 2, identical or different substituents. Examples of substituents which may be mentioned are: alkyl with preferably 1 to 4, in particular 1 or 2, carbon atoms, such as methyl, ethyl and n- and iso-propyl; alkoxy with preferably 1 to 4, in particular 1 or 2, carbon atoms, such as methoxy, ethoxy and n- and iso-propoxy; alkylthio with preferably 1 to 4, in particular 1 or 2, carbon atoms, such as methylthio, ethylthio and n- and iso-propylthio; halogen, preferably fluorine, chlorine, bromine and iodine, in particular chlorine, bromine and iodine; cyano and nitro; and halogenoalkyl, halogenoalkoxy and halogenoalkylthio with preferably 1 to 4, in particular 1 or 2, carbon atoms and 1 to 5, in particular 1 to 3, halogen atoms, such as trifluoromethyl, trifluoromethoxy and trifluoromethylthio.

Preferred compounds of the formula (I) are those in which $X^1$ and $X^2$ are identical or different and represent fluorine, chlorine and/or bromine, $R^1$ represents hydrogen or $C_1$–$C_6$-alkyl, $R^2$ and $R^3$ are identical or different and represent hydrogen, $C_1$–$C_6$-alkyl, $C_1$–$C_4$-halogenoalkyl, 1-pyrazolylmethyl, 1-imidazolylmethyl, 1-(1,2,4-triazolyl)-methyl, $C_1$–$C_4$-alkoxy-$C_1$–$C_4$-alkyl, $C_1$–$C_4$-alkylthio-$C_1$–$C_4$-alkyl, (di)-$C_1$–$C_4$-alkylamino-$C_1$–$C_4$-alkyl, or radicals from the series comprising phenyl, $C_2$–$C_4$-alkenoxy-$C_1$–$C_2$-alkyl and $C_2$–$C_4$-alkinoxy-$C_1$–$C_2$-alkyl which are optionally substituted by halogen, such as, in particular, chlorine, bromine or iodine, $R^4$ represents hydrogen or $C_1$–$C_4$-alkyl, $R^5$ and $R^6$ are identical or different and represent hydrogen, $C_1$–$C_4$-alkyl, or radicals from the series comprising phenyl, benzyl and phenethyl which are optionally substituted by halogen, such as, in particular, chlorine, bromine or iodine, and R represents triiodo-$C_2$–$C_4$-alkenyl, dibromo-iodo-$C_2$–$C_4$-alkenyl, dichloro-iodo-$C_2$–$C_4$-alkenyl, $C_2$–$C_4$-alkinyl or iodo-$C_2$–$C_4$-alkinyl.

The invention particularly relates to compounds of the formula (I) in which $X^1$ and $X^2$ are identical or different and represent chlorine and/or bromine, $R^1$ represents hydrogen, methyl, ethyl, n-propyl or n-butyl, $R^2$ and $R^3$ are identical or different and represent hydrogen, methyl, ethyl, n-propyl, n-butyl, 1-pyrazolylmethyl, 1-imidazolylmethyl, 1-(1,2,4-triazolyl)-methyl, methoxymethyl, ethoxymethyl, ethoxyethyl, methylthiomethyl, ethylthiomethyl, ethylthioethyl, (di)-methylaminomethyl, (di)methylaminoethyl, (di)ethylaminomethyl, (di)ethylaminoethyl, propenyloxymethyl, propinyloxymethyl, iodopropinyloxymethyl, triiodopropenyloxymethyl, dichloroiodopropenyloxymethyl, dibromoiodopropenyloxymethyl, phenyl, 2-, 3-, 4-chlorophenyl, 2,4-dichlorophenyl, 2-, 3-, 4-bromophenyl, 2,4-dibromophenyl, chloromethyl or bromomethyl, R[4] represents hydrogen, methyl, ethyl or n- or i-propyl, R[5] and R[6] are identical or different and represent hydrogen, methyl, ethyl, n-propyl, i-propyl, 2-, 3-, 4-chlorophenyl, 2,4-dichlorophenyl or 4-bromophenyl and R represents triiodoethenyl, dichloroiodoethenyl, dibromoiodoethenyl, ethinyl, iodoethinyl, propinyl or iodopropinyl.

Very particularly preferred compounds of the formula (I) are those
in which

X[1] and X[2] are identical or different and represent chlorine and/or bromine,

R[1] represents hydrogen, methyl or ethyl,

R[2] and R[3] are identical or different and represent hydrogen, methyl, ethyl, chloromethyl, bromomethyl, 1-propenyloxymethyl, 1-propinyloxymethyl or 1-iodopropinyloxymethyl, R[4] represents hydrogen or methyl, R[5] and R[6] are identical or different and represent hydrogen or methyl and R[7] represents triiodoethyl, dichloroiodoethyl, dibromoiodoethyl, ethinyl or iodoethinyl.

If 2,2-dichlorocyclopropylmethyl bromide and 1-propin-3-ol are used for process variant (a) as starting substances for the compounds of the formula (Ia), the reaction can be outlined by the following equation:

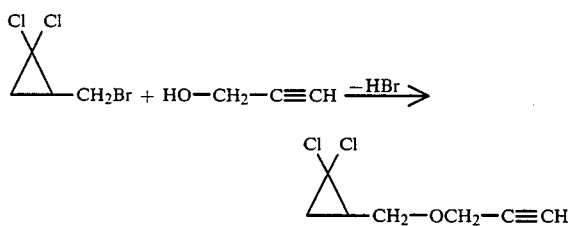

If 3-(2,2-dichloro-cyclopropylmethoxy)-1-propine and iodine are used for process variant (b) as starting substances for the compounds of the formula (Ib), the reaction can be outlined by the following equations:

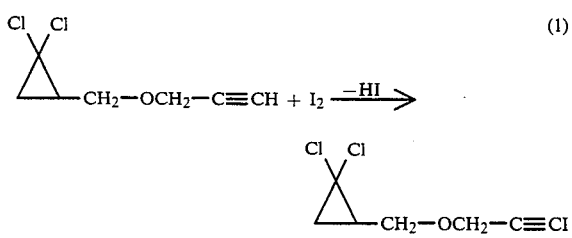

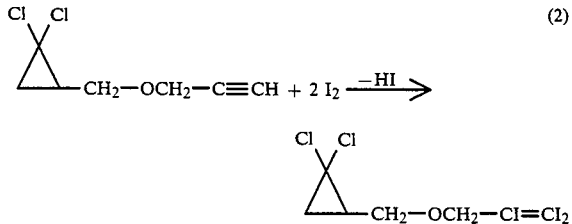

If 3-(2,2-dichloro-cyclopropylmethoxy)-1-iodo-1-propine and chlorine are used as starting substances for process variant (c), the reaction can be outlined by the following equation:

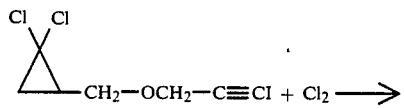

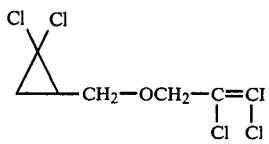

Formula (II) provides a definition of the cyclopropylmethyl(ene) halides to be used as starting substances in process variant (a) according to the invention. In this formula, $X^1$, $X^2$, $R^1$, $R^2$, $R^3$ and $R^4$ represent those radicals which have been given above in the definition of the formula (I). Hal in this formula (II) represents halogen, in particular chlorine, bromine or iodine.

Examples of compounds of the formula (II) which may be mentioned are:

TABLE 1

Hal = chlorine, bromine or iodine

| $X^1$ | $X^2$ | $R^1$ | $R^2$ | $R_3$ | $R^4$ |
|---|---|---|---|---|---|
| Cl | Cl | H | CH$_3$ | H | H |
| Br | Br | H | CH$_3$ | H | H |
| Cl | Cl | H | H | H | H |
| Br | Br | H | H | H | H |
| Cl | Cl | H | H | CH$_3$ | H |
| Br | Br | H | H | CH$_3$ | H |
| Cl | Cl | H | CH$_3$ | CH$_3$ | H |
| Br | Br | H | CH$_3$ | CH$_3$ | H |
| Cl | CL | H | CH$_3$ | CH$_3$ | CH$_3$ |
| Br | Br | H | CH$_3$ | CH$_3$ | CH$_3$ |
| Cl | Cl | H | H | H | CH$_3$ |
| Br | Br | H | H | H | CH$_3$ |
| Cl | Cl | H | CH$_3$ | H | CH$_3$ |
| Br | Br | H | CH$_3$ | H | CH$_3$ |
| Cl | Cl | H | H | CH$_3$ | CH$_3$ |
| Br | Br | H | H | CH$_3$ | CH$_3$ |
| Cl | Cl | H | CH$_2$Cl | H | H |
| Br | Br | H | CH$_2$Cl | H | H |
| Cl | Cl | H | CH$_2$Br | H | H |
| Br | Br | H | CH$_2$Br | H | H |
| Cl | Cl | H | H | CH$_2$Cl | H |
| Br | Br | H | H | CH$_2$Cl | H |
| Cl | Cl | H | H | CH$_2$Br | H |
| Br | Br | H | H | CH$_2$Br | H |
| Cl | Cl | H | IC≡CH—CH$_2$OCH$_2$— | H | H |
| Br | Br | H | IC≡CH—CH$_2$OCH$_2$— | H | H |
| Cl | Cl | H | HC≡C—CH$_2$OCH$_2$— | H | H |
| Br | Br | H | HC≡C—CH$_2$OCH$_2$— | H | H |
| Cl | Cl | H | 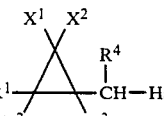 | H | H |
| Br | Br | H |  | H | H |
| Cl | Cl | CH$_3$ | CH$_3$ | H | H |
| Br | Br | CH$_3$ | CH$_3$ | H | H |
| Cl | Cl | CH$_3$ | CH$_3$ | H | CH$_3$ |
| Br | Br | CH$_3$ | CH$_3$ | H | CH$_3$ |

Compounds of the formula (II) are known and can be prepared in the customary manner by processes which are known per se (compare Angew. Chem. Int. Ed. 16, 493 (1977) Verlag Chemie, Weinheim and 'Phase Transfer Catalysis' 1980, Verlag Chemie, Weinheim).

Formula (III) provides a definition of the alcohols also to be used as starting substances in process variant (a). In this formula, $R^5$, $R^6$ and $R'$ represent those radicals which have been mentioned above in the definition of formula (I) or (III).

Possible salts of the compounds of the formula III are the alkali metal or alkaline earth metal salts, such as sodium, calcium salts or potassium salts (if appropriate obtained in situ).

Examples which may be mentioned of compounds of the formula (III) are:

TABLE 2

$$HO-\underset{R^6}{\overset{R^5}{\underset{|}{\overset{|}{C}}}}-R' \quad (III)$$

HO—CH₂—C≡CH
HO—CH(CH₃)—C≡CH
HO—C(CH₃)₂—C≡CH

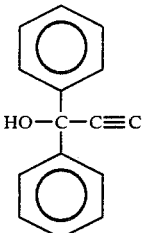
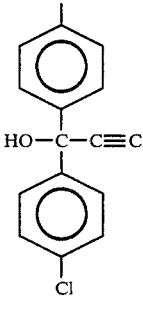
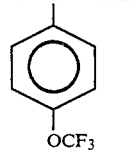
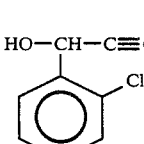
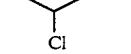
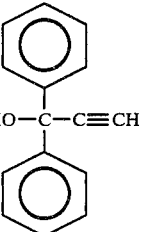
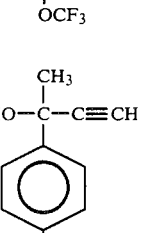
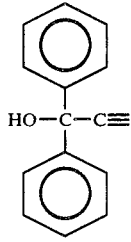
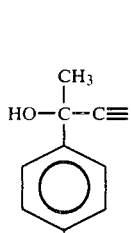
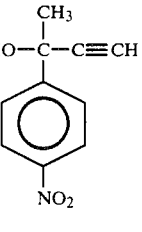
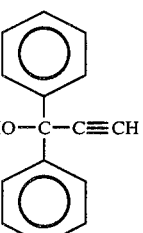
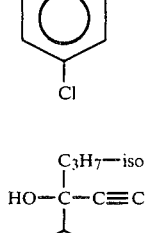

TABLE 2-continued $$HO-\underset{R^6}{\overset{R^5}{\underset{|}{\overset{|}{C}}}}-R' \quad (III)$$

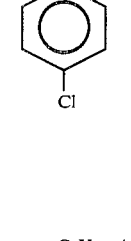
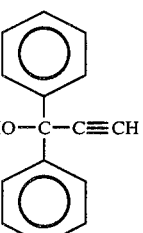
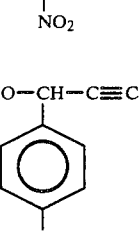
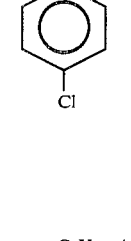
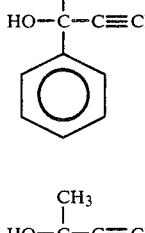
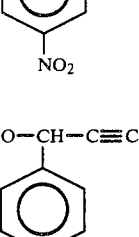
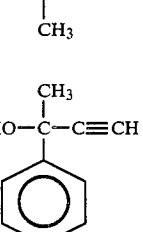
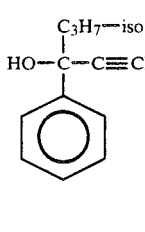
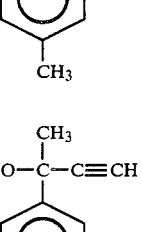
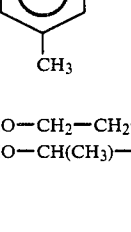
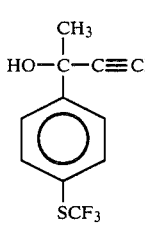
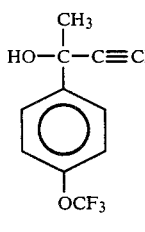
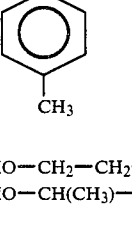

HO—CH₂—CH₂—C≡CH
HO—CH(CH₃)—CH₂—C≡CH

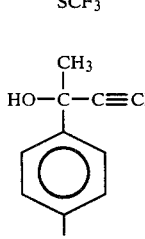

TABLE 2-continued

Structural formula (III):
$$HO-\underset{R^6}{\overset{R^5}{\underset{|}{C}}}-R'$$

(Table contains chemical structure drawings of various propargyl alcohol derivatives with substituted phenyl groups.)

TABLE 2-continued $$\begin{array}{c} R^5 \\ | \\ HO-C-R' \\ | \\ R^6 \end{array} \quad (III)$$

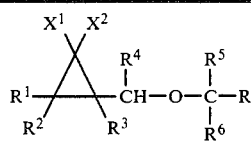

Alcohols of the formula (III) are known and can be prepared in a customary manner by processes which are known per se (compare DE-AS (German Published Specification) 1,217,368; J. Agr. Food Chem. 18, 78 (1970); Liebigs Ann Chem. 308, 264 (1899) and 682, 62 (1965); Angew. Chem. 71, 245 (1959); J. Am. Chem. Soc. 83, 4,990 (1961); Bull. Soc. Chim. France 911 (1969) and DE-OS (German Published Specification) 3,122,176.

Possible diluents in process variant (a) are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chclorobenzene and o-dichlorobenzene, and furthermore ethers, such as diethyl ether, dibutyl ether, glycol dimethyl ether, diglycol dimethyl ether, tetrahydrofuran and dioxane, and also ketones, such as acetone, methyl ethyl ketone, methyl isopropyl ketone and methyl isobutyl ketone, as well as esters, such as methyl acetate and ethyl acetate, and furthermore nitriles, such as, for example, acetonitrile ad propionitrile, and moreover amides, such as, for example, dimethylformamide, dimethylacetamide and N-methylpyrrolidone, as well as dimethylsulphoxide, tetramethylene sulphone and hexamethylphosphoric acid triamide.

All the customary acid-binding agents can be used as acid acceptors in process variant (a). Preferred acid-binding agents include alkali metal carbonates, hydrides, hydroxides and alcoholates, such as sodium carbonate and potassium carbonate, sodium hydride, sodium hydroxide, sodium methylate or ethylate and potassium methylate or ethylate, and furthermore aliphatic, aromatic or heterocyclic amines, for example trimethylamine, triethylamine, dimethylaniline, dimethylbenzylamine and pyridine.

The reaction temperature is kept between about −20° C. and +90° C., preferably between 0° C. and +80° C., in process variaant (a) according to the invention. The process is preferably carried out under normal pressure.

In carrying out process variant (a) according to the invention, 1, to 3 moles, preferably 1 to 2 moles of the compound of the formula (III) are reacted per mole of compound of the formula (II). In general, the process according to the invention is carried out as follows:

An acid acceptor is added to the initially introduced alcohol of the formula (III), and the compound of the formula (II) is added in portions. After the reaction, the compound of the formula (Ia) is isolated and purified in the customary manner.

Formula (Ia) provides a definition of the compounds to be used as starting substances in process variant (b) according to the invention. In this formula, $X^1$, $X^2$, $R^2$, $R^3$, $R^4$, $R^5$ and $R^6$ represent those radicals which have been mentioned above in the definition of the formula (I). $R'$ in this formula (Ia) preferably represents $C_2$-$C_4$-alkinyl.

Examples which may be mentioned of compounds of the formula (Ia) are:

TABLE 3

$$\begin{array}{c} X^1 \;\; X^2 \\ \diagdown\!\diagup \\ R^1\!\!-\!\!\diagup\diagdown\!\!-\!\!CH-O-\overset{\overset{R^4}{|}}{\underset{\underset{R^6}{|}}{C}}-R' \\ R^2 \quad R^3 \quad R^5 \end{array} \quad (Ia)$$

| $X^1$ | $X^2$ | $R^1$ | $R^2$ | $R^3$ | $R^4$ | $-CR^5R^6R'$ |
|---|---|---|---|---|---|---|
| Cl | Cl | H | $CH_3$ | H | H | $-CH_2-C\equiv CH$ |
| Br | Br | H | $CH_3$ | H | H | $-CH_2-C\equiv CH$ |
| Cl | Cl | H | H | H | H | $-CH_2-C\equiv CH$ |
| Br | Br | H | H | H | H | $-CH_2-C\equiv CH$ |
| Cl | Cl | H | H | $CH_3$ | H | $-CH_2-C\equiv CH$ |
| Br | Br | H | H | $CH_3$ | H | $-CH_2-C\equiv CH$ |
| Cl | Cl | H | $CH_3$ | $CH_3$ | H | $-CH_2-C\equiv CH$ |
| Br | Br | H | $CH_3$ | $CH_3$ | H | $-CH_2-C\equiv CH$ |
| Cl | Cl | H | $CH_3$ | $CH_3$ | $CH_3$ | $-CH_2-C\equiv CH$ |
| Br | Br | H | $CH_3$ | $CH_3$ | $CH_3$ | $-CH_2-C\equiv CH$ |
| Cl | Cl | H | H | H | $CH_3$ | $-CH_2-C\equiv CH$ |
| Br | Br | H | H | H | $CH_3$ | $-CH_2-C\equiv CH$ |
| Cl | Cl | H | $CH_3$ | H | $CH_3$ | $-CH_2-C\equiv CH$ |
| Br | Br | H | $CH_3$ | H | $CH_3$ | $-CH_2-C\equiv CH$ |
| Cl | Cl | H | H | $CH_3$ | $CH_3$ | $-CH_2-C\equiv CH$ |
| Br | Br | H | H | $CH_3$ | $CH_3$ | $-CH_2-C\equiv CH$ |
| Cl | Cl | H | $CH_2Cl$ | H | H | $-CH_2-C\equiv CH$ |
| Br | Br | H | $CH_2Cl$ | H | H | $-CH_2-C\equiv CH$ |
| Cl | Cl | H | $CH_2Br$ | H | H | $-CH_2-C\equiv CH$ |
| Br | Br | H | $CH_2Br$ | H | H | $-CH_2-C\equiv CH$ |
| Cl | Cl | H | H | $CH_2Cl$ | H | $-CH_2-C\equiv CH$ |
| Br | Br | H | H | $CH_2Cl$ | H | $-CH_2-C\equiv CH$ |
| Cl | Cl | H | H | $CH_2Br$ | H | $-CH_2-C\equiv CH$ |
| Br | Br | H | H | $CH_2Br$ | H | $-CH_2-C\equiv CH$ |

TABLE 3-continued

(Ia)

| X¹ | X² | R¹ | R² | R³ | R⁴ | —CR⁵R⁶R' |
|---|---|---|---|---|---|---|
| Cl | Cl | H | $H_2C=CH-CH_2OCH_2-$ | H | H | $-CH_2-C\equiv CH$ |
| Br | Br | H | $H_2C=CH-CH_2OCH_2-$ | H | H | $-CH_2-C\equiv CH$ |
| Cl | Cl | H | $HC\equiv C-CH_2OCH_2-$ | H | H | $-CH_2-C\equiv CH$ |
| Br | Br | H | $HC\equiv C-CH_2OCH_2-$ | H | H | $-CH_2-C\equiv CH$ |
| Cl | Cl | H | $C_6H_5$ | H | H | $-CH_2-C\equiv CH$ |
| Br | Br | H | $C_6H_5$ | H | H | $-CH_2-C\equiv CH$ |
| Cl | Cl | $CH_3$ | $CH_3$ | H | H | $-CH_2-C\equiv CH$ |
| Br | Br | $CH_3$ | $CH_3$ | H | H | $-CH_2-C\equiv CH$ |
| Cl | Cl | $CH_3$ | $CH_3$ | H | $CH_3$ | $-CH_2-C\equiv CH$ |
| Br | Br | $CH_3$ | $CH_3$ | H | $CH_3$ | $-CH_2-C\equiv CH$ |
| Cl | Cl | H | $CH_3$ | H | H | $-CH(CH_3)-C\equiv CH$ |
| Br | Br | H | $CH_3$ | H | H | $-CH(CH_3)-C\equiv CH$ |
| Cl | Cl | H | H | H | H | $-CH(CH_3)-C\equiv CH$ |
| Br | Br | H | H | H | H | $-CH(CH_3)-C\equiv CH$ |
| Cl | Cl | H | H | $CH_3$ | H | $-CH(CH_3)-C\equiv CH$ |
| Br | Br | H | H | $CH_3$ | H | $-CH(CH_3)-C\equiv CH$ |
| Cl | Cl | H | $CH_3$ | $CH_3$ | H | $-CH(CH_3)-C\equiv CH$ |
| Br | Br | H | $CH_3$ | $CH_3$ | H | $-CH(CH_3)-C\equiv CH$ |
| Cl | Cl | H | $CH_3$ | $CH_3$ | $CH_3$ | $-CH(CH_3)-C\equiv CH$ |
| Br | Br | H | $CH_3$ | $CH_3$ | $CH_3$ | $-CH(CH_3)-C\equiv CH$ |
| Cl | Cl | H | H | $CH_3$ | $CH_3$ | $-CH(CH_3)-C\equiv CH$ |
| Br | Br | H | H | $CH_3$ | $CH_3$ | $-CH(CH_3)-C\equiv CH$ |
| Cl | Cl | H | $CH_3$ | H | $CH_3$ | $-CH(CH_3)-C\equiv CH$ |
| Br | Br | H | $CH_3$ | H | $CH_3$ | $-CH(CH_3)-C\equiv CH$ |
| Cl | Cl | H | H | $CH_3$ | $CH_3$ | $-CH(CH_3)-C\equiv CH$ |
| Br | Br | H | H | $CH_3$ | $CH_3$ | $-CH(CH_3)-C\equiv CH$ |
| Cl | Cl | H | $CH_2Cl$ | H | H | $-CH(CH_3)-C\equiv CH$ |
| Br | Br | H | $CH_2Cl$ | H | H | $-CH(CH_3)-C\equiv CH$ |
| Cl | Cl | H | $CH_2Br$ | H | H | $-CH(CH_3)-C\equiv CH$ |
| Br | Br | H | $CH_2Br$ | H | H | $-CH(CH_3)-C\equiv CH$ |
| Cl | Cl | H | H | $CH_2Cl$ | H | $-CH(CH_3)-C\equiv CH$ |
| Br | Br | H | H | $CH_2Cl$ | H | $-CH(CH_3)-C\equiv CH$ |
| Cl | Cl | H | H | $CH_2Br$ | H | $-CH(CH_3)-C\equiv CH$ |
| Br | Br | H | H | $CH_2Br$ | H | $-CH(CH_3)-C\equiv CH$ |
| Cl | Cl | H | $H_2C=CH-CH_2OCH_2-$ | H | H | $-CH(CH_3)-C\equiv CH$ |
| Br | Br | H | $H_2C=CH-CH_2OCH_2-$ | H | H | $-CH(CH_3)-C\equiv CH$ |
| Cl | Cl | H | $HC\equiv C-CH_2OCH_2-$ | H | H | $-CH(CH_3)-C\equiv CH$ |
| Br | Br | H | $HC\equiv C-CH_2OCH_2-$ | H | H | $-CH(CH_3)-C\equiv CH$ |
| Cl | Cl | H | $C_6H_5$ | H | H | $-CH(CH_3)-C\equiv CH$ |
| Br | Br | H | $C_6H_5$ | H | H | $-CH(CH_3)-C\equiv CH$ |
| Cl | Cl | $CH_3$ | $CH_3$ | H | H | $-CH(CH_3)-C\equiv CH$ |
| Br | Br | $CH_3$ | $CH_3$ | H | H | $-CH(CH_3)-C\equiv CH$ |
| Cl | Cl | $CH_3$ | $CH_3$ | H | $CH_3$ | $-CH(CH_3)-C\equiv CH$ |
| Br | Br | $CH_3$ | $CH_3$ | H | $CH_3$ | $-CH(CH_3)-C\equiv CH$ |

TABLE 3-continued
(Ia)
$$\begin{array}{c} X^1\ X^2 \\ R^1 \diagdown \diagup R^4 \\ \phantom{R^1}\diagdown\phantom{R^4}CH-O-\overset{R^5}{\underset{R^6}{C}}-R' \\ R^2\phantom{XX}R^3 \end{array}$$
| X¹ | X² | R¹ | R² | R³ | R⁴ | —CR⁵R⁶R' |
|----|----|----|----|----|----|----------|
| Cl | Cl | H | CH₃ | H | H | 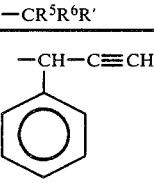 |
| Br | Br | H | CH₃ | H | H | 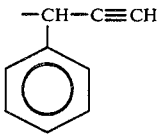 |
| Cl | Cl | H | H | H | H | 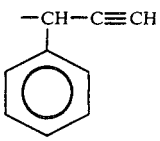 |
| Br | Br | H | H | H | H | 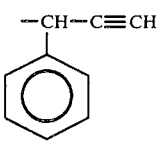 |
| Cl | Cl | H | H | CH₃ | H | 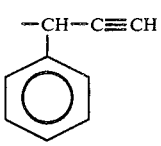 |
| Br | Br | H | H | CH₃ | H | 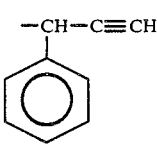 |
| Cl | Cl | H | CH₃ | CH₃ | H | 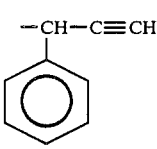 |
| Br | Br | H | CH₃ | CH₃ | H | 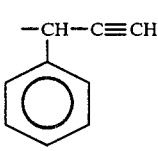 |
| Cl | Cl | H | CH₃ | CH₃ | CH₃ | 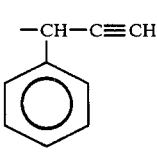 |

TABLE 3-continued $$\text{(Ia)}$$

Structure: cyclopropane with X¹, X² on one carbon; R¹, R² on another; R³, R⁴ on the CH; -CH-O-C(R⁵)(R⁶)-R'

| X¹ | X² | R¹ | R² | R³ | R⁴ | —CR⁵R⁶R' |
|----|----|----|-----|-----|-----|----------|
| Br | Br | H | CH₃ | CH₃ | CH₃ | —CH(C₆H₅)—C≡CH |
| Cl | Cl | H | H | H | CH₃ | —CH(C₆H₅)—C≡CH |
| Br | Br | H | H | H | CH₃ | —CH(C₆H₅)—C≡CH |
| Cl | Cl | H | CH₃ | H | CH₃ | —CH(C₆H₅)—C≡CH |
| Br | Br | H | CH₃ | H | CH₃ | —CH(C₆H₅)—C≡CH |
| Cl | Cl | H | H | CH₃ | CH₃ | —CH(C₆H₅)—C≡CH |
| Br | Br | H | H | CH₃ | CH₃ | —CH(C₆H₅)—C≡CH |
| Cl | Cl | H | CH₂Cl | H | H | —CH(C₆H₅)—C≡CH |
| Br | Br | H | CH₂Cl | H | H | —CH(C₆H₅)—C≡CH |

TABLE 3-continued $$\underset{R^2\ \ \ \ R^3}{\overset{X^1\ \ X^2}{\triangle}}\underset{}{\overset{R^4}{\underset{}{CH}}-O-\underset{R^6}{\overset{R^5}{\underset{}{C}}}-R' \tag{Ia}$$

| X¹ | X² | R¹ | R² | R³ | R⁴ | —CR⁵R⁶R' |
|---|---|---|---|---|---|---|
| Cl | Cl | H | CH₂Br | H | H | —CH—C≡CH, phenyl |
| Br | Br | H | CH₂Br | H | H | —CH—C≡CH, phenyl |
| Cl | Cl | H | H | CH₂Cl | H | —CH—C≡CH, phenyl |
| Br | Br | H | H | CH₂Cl | H | —CH—C≡CH, phenyl |
| Cl | Cl | H | H | CH₂Br | H | —CH—C≡CH, phenyl |
| Br | Br | H | H | CH₂Br | H | —CH—C≡CH, phenyl |
| Cl | Cl | H | H₂C=CH—CH₂OCH₂— | H | H | —CH—C≡CH, phenyl |
| Br | Br | H | H₂C=CH—CH₂OCH₂— | H | H | —CH—C≡CH, phenyl |
| Cl | Cl | H | HC≡C—CH₂OCH₂— | H | H | —CH—C≡CH, phenyl |

TABLE 3-continued $$\begin{array}{c} X^1\ X^2 \\ R^1 \diagdown\!\!\!\diagup R^4\ R^5 \\ \phantom{R^1}\diagup\!\!\!\diagdown\ |\ \ |\ \ \\ R^2\ \ R^3\ CH-O-C-R' \\ \phantom{R^2\ \ R^3\ CH-O-}|\ \\ \phantom{R^2\ \ R^3\ CH-O-}R^6 \end{array}$$ (Ia)

| $X^1$ | $X^2$ | $R^1$ | $R^2$ | $R^3$ | $R^4$ | $-CR^5R^6R'$ |
|---|---|---|---|---|---|---|
| Br | Br | H | HC≡C—CH$_2$OCH$_2$— | H | H | —CH(C$_6$H$_5$)—C≡CH |
| Cl | Cl | H | C$_6$H$_5$ | H | H | —CH(C$_6$H$_5$)—C≡CH |
| Br | Br | H | C$_6$H$_5$ | H | H | —CH(C$_6$H$_5$)—C≡CH |
| Cl | Cl | CH$_3$ | CH$_3$ | H | H | —CH(C$_6$H$_5$)—C≡CH |
| Br | Br | CH$_3$ | CH$_3$ | H | H | —CH(C$_6$H$_5$)—C≡CH |
| Cl | Cl | CH$_3$ | CH$_3$ | H | CH$_3$ | —CH(C$_6$H$_5$)—C≡CH |
| Br | Br | CH$_3$ | CH$_3$ | H | CH$_3$ | —CH(C$_6$H$_5$)—C≡CH |
| Cl | Cl | H | CH$_3$ | H | H | —CH(C$_2$H$_5$)—C≡CH |
| Br | Br | H | CH$_3$ | H | H | —CH(C$_2$H$_5$)—C≡CH |
| Cl | Cl | H | H | H | H | —CH(C$_2$H$_5$)—C≡CH |
| Br | Br | H | H | H | H | —CH(C$_2$H$_5$)—C≡CH |
| Cl | Cl | H | H | CH$_3$ | H | —CH(C$_2$H$_5$)—C≡CH |
| Br | Br | H | H | CH$_3$ | H | —CH(C$_2$H$_5$)—C≡CH |
| Cl | Cl | H | CH$_3$ | CH$_3$ | H | —CH(C$_2$H$_5$)—C≡CH |
| Br | Br | H | CH$_3$ | CH$_3$ | H | —CH(C$_2$H$_5$)—C≡CH |
| Cl | Cl | H | CH$_3$ | CH$_3$ | CH$_3$ | —CH(C$_2$H$_5$)—C≡CH |
| Br | Br | H | CH$_3$ | CH$_3$ | CH$_3$ | —CH(C$_2$H$_5$)—C≡CH |
| Cl | Cl | H | H | H | CH$_3$ | —CH(C$_2$H$_5$)—C≡CH |
| Br | Br | H | H | H | CH$_3$ | —CH(C$_2$H$_5$)—C≡CH |
| Cl | Cl | H | CH$_3$ | H | CH$_3$ | —CH(C$_2$H$_5$)—C≡CH |
| Br | Br | H | CH$_3$ | H | CH$_3$ | —CH(C$_2$H$_5$)—C≡CH |
| Cl | Cl | H | H | CH$_3$ | CH$_3$ | —CH(C$_2$H$_5$)—C≡CH |
| Br | Br | H | H | CH$_3$ | CH$_3$ | —CH(C$_2$H$_5$)—C≡CH |
| Cl | Cl | H | CH$_2$Cl | H | H | —CH(C$_2$H$_5$)—C≡CH |
| Br | Br | H | CH$_2$Cl | H | H | —CH(C$_2$H$_5$)—C≡CH |

TABLE 3-continued (Ia)

$$\begin{array}{c} X^1\ X^2 \\ R^1 \diagdown\!\!\!\diagup R^4\ R^5 \\ \phantom{R^1}\diagup\!\!\!\diagdown\!\!\!| \phantom{X}|\phantom{X}| \\ R^2\ R^3\ CH-O-C-R' \\ \phantom{XXXXXXXX}R^6 \end{array}$$

| $X^1$ | $X^2$ | $R^1$ | $R^2$ | $R^3$ | $R^4$ | $-CR^5R^6R'$ |
|---|---|---|---|---|---|---|
| Cl | Cl | H | $CH_2Br$ | H | H | $-CH(C_2H_5)-C\equiv CH$ |
| Br | Br | H | $CH_2Br$ | H | H | $-CH(C_2H_5)-C\equiv CH$ |
| Cl | Cl | H | H | $CH_2Cl$ | H | $-CH(C_2H_5)-C\equiv CH$ |
| Br | Br | H | H | $CH_2Cl$ | H | $-CH(C_2H_5)-C\equiv CH$ |
| Cl | Cl | H | H | $CH_2Br$ | H | $-CH(C_2H_5)-C\equiv CH$ |
| Br | Br | H | H | $CH_2Br$ | H | $-CH(C_2H_5)-C\equiv CH$ |
| Cl | Cl | H | $H_2C=CH-CH_2OCH_2-$ | H | H | $-CH(C_2H_5)-C\equiv CH$ |
| Br | Br | H | $H_2C=CH-CH_2OCH_2-$ | H | H | $-CH(C_2H_5)-C\equiv CH$ |
| Cl | Cl | H | $HC\equiv C-CH_2OCH_2-$ | H | H | $-CH(C_2H_5)-C\equiv CH$ |
| Br | Br | H | $HC\equiv C-CH_2OCH_2-$ | H | H | $-CH(C_2H_5)-C\equiv CH$ |
| Cl | Cl | H |  | H | H | $-CH(C_2H_5)-C\equiv CH$ |
| Br | Br | H |  | H | H | $-CH(C_2H_5)-C\equiv CH$ |
| Cl | Cl | $CH_3$ | $CH_3$ | H | H | $-CH(C_2H_5)-C\equiv CH$ |
| Br | Br | $CH_3$ | $CH_3$ | H | H | $-CH(C_2H_5)-C\equiv CH$ |
| Cl | Cl | $CH_3$ | $CH_3$ | H | $CH_3$ | $-CH(C_2H_5)-C\equiv CH$ |
| Br | Br | $CH_3$ | $CH_3$ | H | $CH_3$ | $-CH(C_2H_5)-C\equiv CH$ |
| Cl | Cl | H | $CH_3$ | H | H |  |
| Br | Br | H | $CH_3$ | H | H | 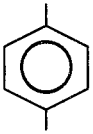 |
| Cl | Cl | H | H | H | H | 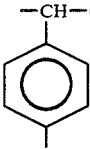 |
| Br | Br | H | H | H | H | 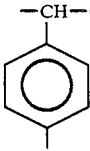 |

TABLE 3-continued (Ia)

Structure: cyclopropane with $X^1$, $X^2$ on one carbon, $R^1$, $R^2$ on another, $R^3$ on the third bearing $-CH(R^4)-O-C(R^5)(R^6)-R'$

| $X^1$ | $X^2$ | $R^1$ | $R^2$ | $R^3$ | $R^4$ | $-CR^5R^6R'$ |
|---|---|---|---|---|---|---|
| Cl | Cl | H | H | CH₃ | H | -CH-C≡CH, 4-Cl-C₆H₄ |
| Br | Br | H | H | CH₃ | H | -CH-C≡CH, 4-Cl-C₆H₄ |
| Cl | Cl | H | CH₃ | CH₃ | H | -CH-C≡CH, 4-Cl-C₆H₄ |
| Br | Br | H | CH₃ | CH₃ | H | -CH-C≡CH, 4-Cl-C₆H₄ |
| Cl | Cl | H | CH₃ | CH₃ | CH₃ | -CH-C≡CH, 4-Cl-C₆H₄ |
| Br | Br | H | CH₃ | CH₃ | CH₃ | -CH-C≡CH, 4-Cl-C₆H₄ |
| Cl | Cl | H | H | H | CH₃ | -CH-C≡CH, 4-Cl-C₆H₄ |

TABLE 3-continued (Ia)

structure: cyclopropane with X¹, X² on one carbon; R¹, R² on another; R³, R⁴ on third with CH—O—C(R⁵)(R⁶)—R'

| X¹ | X² | R¹ | R² | R³ | R⁴ | —CR⁵R⁶R' |
|----|----|----|----|----|----|----------|
| Br | Br | H | H | H | CH₃ | —CH—C≡CH, 4-Cl-C₆H₄ |
| Cl | Cl | H | CH₃ | H | CH₃ | —CH—C≡CH, 4-Cl-C₆H₄ |
| Br | Br | H | CH₃ | H | CH₃ | —CH—C≡CH, 4-Cl-C₆H₄ |
| Cl | Cl | H | H | CH₃ | CH₃ | —CH—C≡CH, 4-Cl-C₆H₄ |
| Br | Br | H | H | CH₃ | CH₃ | —CH—C≡CH, 4-Cl-C₆H₄ |
| Cl | Cl | H | CH₂Cl | H | H | —CH—C≡CH, 4-Cl-C₆H₄ |
| Br | Br | H | CH₂Cl | H | H | —CH—C≡CH, 4-Cl-C₆H₄ |

TABLE 3-continued
(Ia)
$$\begin{array}{c} X^1\ X^2 \\ R^1 \underset{R^2}{\overset{R^4}{\diagdown}} \underset{R^3}{\overset{}{\diagup}} CH-O-\underset{R^6}{\overset{R^5}{\underset{|}{C}}}-R' \end{array}$$
| $X^1$ | $X^2$ | $R^1$ | $R^2$ | $R^3$ | $R^4$ | $-CR^5R^6R'$ |
|---|---|---|---|---|---|---|
| Cl | Cl | H | CH₂Br | H | H | 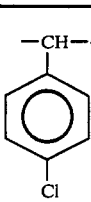 |
| Br | Br | H | CH₂Br | H | H | 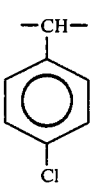 |
| Cl | Cl | H | H | CH₂Cl | H | 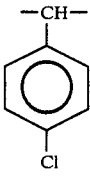 |
| Br | Br | H | H | CH₂Cl | H | 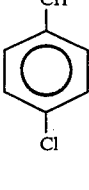 |
| Cl | Cl | H | H | CH₂Br | H | 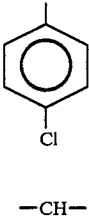 |
| Br | Br | H | H | CH₂Br | H | 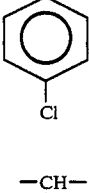 |
| Cl | Cl | H | H₂C=CH—CH₂OCH₂— | H | H |  |

TABLE 3-continued $$\underset{\substack{R^1\\R^2}}{\overset{\substack{X^1\;X^2}}{\triangle}}\underset{R^3}{\overset{R^4}{\underset{|}{C}H}}-O-\underset{\substack{|\\R^6}}{\overset{\substack{R^5\\|}}{C}}-R' \qquad (Ia)$$

| $X^1$ | $X^2$ | $R^1$ | $R^2$ | $R^3$ | $R^4$ | $-CR^5R^6R'$ |
|---|---|---|---|---|---|---|
| Br | Br | H | H₂C=CH—CH₂OCH₂— | H | H | —CH—C≡CH, 4-Cl-C₆H₄ |
| Cl | Cl | H | HC≡C—CH₂OCH₂— | H | H | —CH—C≡CH, 4-Cl-C₆H₄ |
| Br | Br | H | HC≡C—CH₂OCH₂— | H | H | —CH—C≡CH, 4-Cl-C₆H₄ |
| Cl | Cl | H | C₆H₅ | H | H | —CH—C≡CH, 4-Cl-C₆H₄ |
| Br | Br | H | C₆H₅ | H | H | —CH—C≡CH, 4-Cl-C₆H₄ |
| Cl | Cl | CH₃ | CH₃ | H | H | —CH—C≡CH, 4-Cl-C₆H₄ |
| Br | Br | CH₃ | CH₃ | H | H | —CH—C≡CH, 4-Cl-C₆H₄ |

TABLE 3-continued $$\text{(Ia)}$$

Structure:
$$\begin{array}{c} X^1\ X^2 \\ \diagdown / \\ \text{C} \\ / \quad \backslash \\ R^1 \quad R^4 \quad R^5 \\ \quad \text{CH—O—C—R'} \\ R^2 \quad R^3 \quad R^6 \end{array}$$

| $X^1$ | $X^2$ | $R^1$ | $R^2$ | $R^3$ | $R^4$ | —$CR^5R^6R'$ |
|---|---|---|---|---|---|---|
| Cl | Cl | CH₃ | CH₃ | H | CH₃ | —CH—C≡CH, phenyl with p-Cl |
| Br | Br | CH₃ | CH₃ | H | CH₃ | —CH—C≡CH, phenyl with p-Cl |
| Cl | Cl | H | CH₃ | H | H | —C(CH₃)—C≡CH, phenyl |
| Br | Br | H | CH₃ | H | H | —C(CH₃)—C≡CH, phenyl |
| Cl | Cl | H | H | H | H | —C(CH₃)—C≡CH, phenyl |
| Br | Br | H | H | H | H | —C(CH₃)—C≡CH, phenyl |
| Cl | Cl | H | H | CH₃ | H | —C(CH₃)—C≡CH, phenyl |
| Br | Br | H | H | CH₃ | H | —C(CH₃)—C≡CH, phenyl |
| Cl | Cl | H | CH₃ | CH₃ | H | —C(CH₃)—C≡CH, phenyl |

TABLE 3-continued (Ia)

$$\text{structure with } X^1, X^2, R^1, R^2, R^3, R^4\text{-CH-O-C}(R^5)(R^6)R'$$

| $X^1$ | $X^2$ | $R^1$ | $R^2$ | $R^3$ | $R^4$ | $-CR^5R^6R'$ |
|---|---|---|---|---|---|---|
| Br | Br | H | CH$_3$ | CH$_3$ | H | —C(CH$_3$)—C≡CH, phenyl |
| Cl | Cl | H | CH$_3$ | CH$_3$ | CH$_3$ | —C(CH$_3$)—C≡CH, phenyl |
| Br | Br | H | CH$_3$ | CH$_3$ | CH$_3$ | —C(CH$_3$)—C≡CH, phenyl |
| Cl | Cl | H | H | H | CH$_3$ | —C(CH$_3$)—C≡CH, phenyl |
| Br | Br | H | H | H | CH$_3$ | —C(CH$_3$)—C≡CH, phenyl |
| Cl | Cl | H | CH$_3$ | H | CH$_3$ | —C(CH$_3$)—C≡CH, phenyl |
| Br | Br | H | CH$_3$ | H | CH$_3$ | —C(CH$_3$)—C≡CH, phenyl |
| Cl | Cl | H | H | CH$_3$ | CH$_3$ | —C(CH$_3$)—C≡CH, phenyl |
| Br | Br | H | H | CH$_3$ | CH$_3$ | —C(CH$_3$)—C≡CH, phenyl |

TABLE 3-continued $$\begin{array}{c} X^1 \quad X^2 \\ R^1 \diagdown \!\!\! \diagup \quad R^4 \quad R^5 \\ R^2 \diagup \!\!\! \diagdown R^3 \!\!\! - \!\!\! CH \!\!\! - \!\!\! O \!\!\! - \!\!\! \underset{R^6}{\overset{|}{C}} \!\!\! - \!\!\! R' \end{array} \quad (Ia)$$

| $X^1$ | $X^2$ | $R^1$ | $R^2$ | $R^3$ | $R^4$ | $-CR^5R^6R'$ |
|---|---|---|---|---|---|---|
| Cl | Cl | H | CH$_2$Cl | H | H | —C(CH$_3$)—C≡CH, phenyl |
| Br | Br | H | CH$_2$Cl | H | H | —C(CH$_3$)—C≡CH, phenyl |
| Cl | Cl | H | CH$_2$Br | H | H | —C(CH$_3$)—C≡CH, phenyl |
| Br | Br | H | CH$_2$Br | H | H | —C(CH$_3$)—C≡CH, phenyl |
| Cl | Cl | H | H | CH$_2$Cl | H | —C(CH$_3$)—C≡CH, phenyl |
| Br | Br | H | H | CH$_2$Cl | H | —C(CH$_3$)—C≡CH, phenyl |
| Cl | Cl | H | H | CH$_2$Br | H | —C(CH$_3$)—C≡CH, phenyl |
| Br | Br | H | H | CH$_2$Br | H | —C(CH$_3$)—C≡CH, phenyl |
| Cl | Cl | H | H$_2$C=CH—CH$_2$OCH$_2$— | H | H | —C(CH$_3$)—C≡CH, phenyl |

TABLE 3-continued $$\begin{array}{c} X^1 \quad X^2 \\ R^1 \diagdown \!\!\! \diagup R^4 \quad R^5 \\ R^2 / \diagdown \! R^3 \, CH\!-\!O\!-\!C\!-\!R' \\ \phantom{R^2 / \diagdown \! R^3} R^6 \end{array} \quad (Ia)$$

| X¹ | X² | R¹ | R² | R³ | R⁴ | —CR⁵R⁶R′ |
|---|---|---|---|---|---|---|
| Br | Br | H | H₂C=CH—CH₂OCH₂— | H | H | —C(CH₃)—C≡CH, phenyl |
| Cl | Cl | H | HC≡C—CH₂OCH₂— | H | H | —C(CH₃)—C≡CH, phenyl |
| Br | Br | H | HC≡C—CH₂OCH₂— | H | H | —C(CH₃)—C≡CH, phenyl |
| Cl | Cl | H | phenyl | H | H | —C(CH₃)—C≡CH, phenyl |
| Br | Br | H | phenyl | H | H | —C(CH₃)—C≡CH, phenyl |
| Cl | Cl | CH₃ | CH₃ | H | H | —C(CH₃)—C≡CH, phenyl |
| Br | Br | CH₃ | CH₃ | H | H | —C(CH₃)—C≡CH, phenyl |
| Cl | Cl | CH₃ | CH₃ | H | CH₃ | —C(CH₃)—C≡CH, phenyl |
| Br | Br | CH₃ | CH₃ | H | CH₃ | —C(CH₃)—C≡CH, phenyl |
| Cl | Cl | H | CH₃ | H | H | —CH₂—CH₂—C≡CH |
| Br | Br | H | CH₃ | H | H | —CH₂—CH₂—C≡CH |
| Cl | Cl | H | H | H | H | —CH₂—CH₂—C≡CH |

TABLE 3-continued $$\text{(Ia)}$$

Structure: cyclopropane with $X^1, X^2$ at top carbon; $R^1, R^2$ on one carbon and $R^3, R^4$ on the other; attached to $-CH-O-C(R^5)(R^6)-R'$

| $X^1$ | $X^2$ | $R^1$ | $R^2$ | $R^3$ | $R^4$ | $-CR^5R^6R'$ |
|---|---|---|---|---|---|---|
| Br | Br | H | H | H | H | $-CH_2-CH_2-C\equiv CH$ |
| Cl | Cl | H | H | $CH_3$ | H | $-CH_2-CH_2-C\equiv CH$ |
| Br | Br | H | H | $CH_3$ | H | $-CH_2-CH_2-C\equiv CH$ |
| Cl | Cl | H | $CH_3$ | $CH_3$ | H | $-CH_2-CH_2-C\equiv CH$ |
| Br | Br | H | $CH_3$ | $CH_3$ | H | $-CH_2-CH_2-C\equiv CH$ |
| Cl | Cl | H | $CH_3$ | $CH_3$ | $CH_3$ | $-CH_2-CH_2-C\equiv CH$ |
| Br | Br | H | $CH_3$ | $CH_3$ | $CH_3$ | $-CH_2-CH_2-C\equiv CH$ |
| Cl | Cl | H | H | H | $CH_3$ | $-CH_2-CH_2-C\equiv CH$ |
| Br | Br | H | H | H | $CH_3$ | $-CH_2-CH_2-C\equiv CH$ |
| Cl | Cl | H | $CH_3$ | H | $CH_3$ | $-CH_2-CH_2-C\equiv CH$ |
| Br | Br | H | $CH_3$ | H | $CH_3$ | $-CH_2-CH_2-C\equiv CH$ |
| Cl | Cl. | H | H | $CH_3$ | $CH_3$ | $-CH_2-CH_2-C\equiv CH$ |
| Br | Br | H | H | $CH_3$ | $CH_3$ | $-CH_2-CH_2-C\equiv CH$ |
| Cl | Cl | H | $CH_2Cl$ | H | H | $-CH_2-CH_2-C\equiv CH$ |
| Br | Br | H | $CH_2Cl$ | H | H | $-CH_2-CH_2-C\equiv CH$ |
| Cl | Cl | H | $CH_2Br$ | H | H | $-CH_2-CH_2-C\equiv CH$ |
| Br | Br | H | $CH_2Br$ | H | H | $-CH_2-CH_2-C\equiv CH$ |
| Cl | Cl | H | H | $CH_2Cl$ | H | $-CH_2-CH_2-C\equiv CH$ |
| Br | Br | H | H | $CH_2Cl$ | H | $-CH_2-CH_2-C\equiv CH$ |
| Cl | Cl | H | H | $CH_2Br$ | H | $-CH_2-CH_2-C\equiv CH$ |
| Br | Br | H | H | $CH_2Br$ | H | $-CH_2-CH_2-C\equiv CH$ |
| Cl | Cl | H | $H_2C=CH-CH_2OCH_2-$ | H | H | $-CH_2-CH_2-C\equiv CH$ |
| Br | Br | H | $H_2C=CH-CH_2OCH_2-$ | H | H | $-CH_2-CH_2-C\equiv CH$ |
| Cl | Cl | H | $HC\equiv C-CH_2OCH_2-$ | H | H | $-CH_2-CH_2-C\equiv CH$ |
| Br | Br | H | $HC\equiv C-CH_2OCH_2-$ | H | H | $-CH_2-CH_2-C\equiv CH$ |
| Cl | Cl | H |  | H | H | $-CH_2-CH_2-C\equiv CH$ |
| Br | Br | H |  | H | H | $-CH_2-CH_2-C\equiv CH$ |
| Cl | Cl | $CH_3$ | $CH_3$ | H | H | $-CH_2-CH_2-C\equiv CH$ |
| Br | Br | $CH_3$ | $CH_3$ | H | H | $-CH_2-CH_2-C\equiv CH$ |
| Cl | Cl | $CH_3$ | $CH_3$ | H | $CH_3$ | $-CH_2-CH_2-C\equiv CH$ |
| Br | Br | $CH_3$ | $CH_3$ | H | $CH_3$ | $-CH_2-CH_2-C\equiv CH$ |
| Cl | Cl | H | $CH_3$ | H | H | $-CH(CH_3)-CH_2-C\equiv CH$ |
| Br | Br | H | $CH_3$ | H | H | $-CH(CH_3)-CH_2-C\equiv CH$ |
| Cl | Cl | H | H | H | H | $-CH(CH_3)-CH_2-C\equiv CH$ |
| Br | Br | H | H | H | H | $-CH(CH_3)-CH_2-C\equiv CH$ |
| Cl | Cl | H | H | $CH_3$ | H | $-CH(CH_3)-CH_2-C\equiv CH$ |
| Br | Br | H | H | $CH_3$ | H | $-CH(CH_3)-CH_2-C\equiv CH$ |
| Cl | Cl | H | $CH_3$ | $CH_3$ | H | $-CH(CH_3)-CH_2-C\equiv CH$ |
| Br | Br | H | $CH_3$ | $CH_3$ | H | $-CH(CH_3)-CH_2-C\equiv CH$ |
| Cl | Cl | H | $CH_3$ | $CH_3$ | $CH_3$ | $-CH(CH_3)-CH_2-C\equiv CH$ |
| Br | Br | H | $CH_3$ | $CH_3$ | $CH_3$ | $-CH(CH_3)-CH_2-C\equiv CH$ |
| Cl | Cl | H | H | H | $CH_3$ | $-CH(CH_3)-CH_2-C\equiv CH$ |
| Br | Br | H | H | H | $CH_3$ | $-CH(CH_3)-CH_2-C\equiv CH$ |
| Cl | Cl | H | $CH_3$ | H | $CH_3$ | $-CH(CH_3)-CH_2-C\equiv CH$ |
| Br | Br | H | $CH_3$ | H | $CH_3$ | $-CH(CH_3)-CH_2-C\equiv CH$ |
| Cl | Cl | H | H | $CH_3$ | $CH_3$ | $-CH(CH_3)-CH_2-C\equiv CH$ |
| Br | Br | H | H | $CH_3$ | $CH_3$ | $-CH(CH_3)-CH_2-C\equiv CH$ |
| Cl | Cl | H | $CH_2Cl$ | H | H | $-CH(CH_3)-CH_2-C\equiv CH$ |
| Br | Br | H | $CH_2Cl$ | H | H | $-CH(CH_3)-CH_2-C\equiv CH$ |
| Cl | Cl | H | $CH_2Br$ | H | H | $-CH(CH_3)-CH_2-C\equiv CH$ |
| Br | Br | H | $CH_2Br$ | H | H | $-CH(CH_3)-CH_2-C\equiv CH$ |
| Cl | Cl | H | H | $CH_2Cl$ | H | $-CH(CH_3)-CH_2-C\equiv CH$ |
| Br | Br | H | H | $CH_2Cl$ | H | $-CH(CH_3)-CH_2-C\equiv CH$ |
| Cl | Cl | H | H | $CH_2Br$ | H | $-CH(CH_3)-CH_2-C\equiv CH$ |
| Br | Br | H | H | $CH_2Br$ | H | $-CH(CH_3)-CH_2-C\equiv CH$ |
| Cl | Cl | H | $H_2C=CH-CH_2OCH_2-$ | H | H | $-CH(CH_3)-CH_2-C\equiv CH$ |
| Br | Br | H | $H_2C=CH-CH_2OCH_2-$ | H | H | $-CH(CH_3)-CH_2-C\equiv CH$ |
| Cl | Cl | H | $HC\equiv C-CH_2OCH_2-$ | H | H | $-CH(CH_3)-CH_2-C\equiv CH$ |
| Br | Br | H | $HC\equiv C-CH_2OCH_2-$ | H | H | $-CH(CH_3)-CH_2-C\equiv CH$ |

TABLE 3-continued
(Ia)
| X¹ | X² | R¹ | R² | R³ | R⁴ | —CR⁵R⁶R' |
|----|----|----|----|----|----|----------|
| Cl | Cl | H |  | H | H | —CH(CH$_3$)—CH$_2$—C≡CH |
| Br | Br | H | 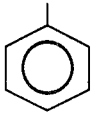 | H | H | —CH(CH$_3$)—CH$_2$—C≡CH |
| Cl | Cl | CH$_3$ | CH$_3$ | H | H | —CH(CH$_3$)—CH$_2$—C≡CH |
| Br | Br | CH$_3$ | CH$_3$ | H | H | —CH(CH$_3$)—CH$_2$—C≡CH |
| Cl | Cl | CH$_3$ | CH$_3$ | H | CH$_3$ | —CH(CH$_3$)—CH$_2$—C≡CH |
| Br | Br | CH$_3$ | CH$_3$ | H | CH$_3$ | —CH(CH$_3$)—CH$_2$—C≡CH |
| Cl | Cl | H | CH$_3$ | H | H | 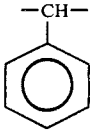 |
| Br | Br | H | CH$_3$ | H | H | 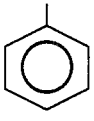 |
| Cl | Cl | H | H | H | H | 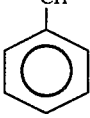 |
| Br | Br | H | H | H | H | 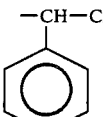 |
| Cl | Cl | H | H | CH$_3$ | H | 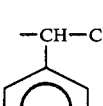 |
| Br | Br | H | H | CH$_3$ | H | 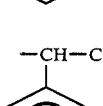 |
| Cl | Cl | H | CH$_3$ | CH$_3$ | H | —CH—CH$_2$—C≡CH (phenyl) |

TABLE 3-continued (Ia)

$$\begin{array}{c} X^1 \quad X^2 \\ \diagdown \diagup \\ R^1 \diagup \diagdown R^4 \quad R^5 \\ \mid \quad \mid \quad \mid \\ R^2 \quad R^3 \quad R^6 \end{array} \text{CH—O—C—R'}$$

| $X^1$ | $X^2$ | $R^1$ | $R^2$ | $R^3$ | $R^4$ | $-CR^5R^6R'$ |
|---|---|---|---|---|---|---|
| Br | Br | H | $CH_3$ | $CH_3$ | H | 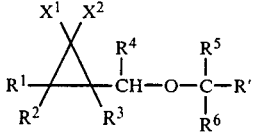 |
| Cl | Cl | H | $CH_3$ | $CH_3$ | $CH_3$ | 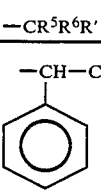 |
| Br | Br | H | $CH_3$ | $CH_3$ | $CH_3$ | 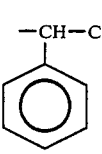 |
| Cl | Cl | H | H | H | $CH_3$ | 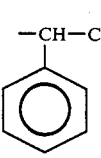 |
| Br | Br | H | H | H | $CH_3$ | 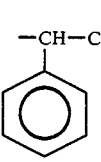 |
| Cl | Cl | H | $CH_3$ | H | $CH_3$ | 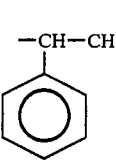 |
| Br | Br | H | $CH_3$ | H | $CH_3$ | 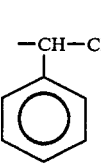 |
| Cl | Cl | H | H | $CH_3$ | $CH_3$ | 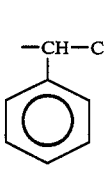 |
| Br | Br | H | H | $CH_3$ | $CH_3$ | 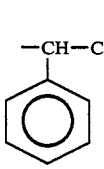 |

TABLE 3-continued $$\text{(Ia)}$$

Structure: cyclopropane with X¹, X² on one carbon; R¹, R² on another; R³ on third; with -CH(R⁴)-O-C(R⁵)(R⁶)-R'

| X¹ | X² | R¹ | R² | R³ | R⁴ | —CR⁵R⁶R' |
|----|----|----|----|----|----|----------|
| Cl | Cl | H | CH₂Cl | H | H | —CH(C₆H₅)—CH₂—C≡CH |
| Br | Br | H | CH₂Cl | H | H | —CH(C₆H₅)—CH₂—C≡CH |
| Cl | Cl | H | CH₂Br | H | H | —CH(C₆H₅)—CH₂—C≡CH |
| Br | Br | H | CH₂Br | H | H | —CH(C₆H₅)—CH₂—C≡CH |
| Cl | Cl | H | H | CH₂Cl | H | —CH(C₆H₅)—CH₂—C≡CH |
| Br | Br | H | H | —CH₂Cl | H | —CH(C₆H₅)—CH₂—C≡CH |
| Cl | Cl | H | H | CH₂Br | H | —CH(C₆H₅)—CH₂—C≡CH |
| Br | Br | H | H | —CH₂Br | H | —CH(C₆H₅)—CH₂—C≡CH |
| Cl | Cl | H | H₂C=CH—CH₂OCH₂— | H | H | —CH(C₆H₅)—CH₂—C≡CH |

TABLE 3-continued (Ia)

$$\underset{R^2}{\overset{R^1}{\diagdown}}\underset{R^3}{\overset{X^1\ X^2}{\diagup}}\underset{R^3}{\overset{R^4}{\diagdown}}CH-O-\underset{R^6}{\overset{R^5}{\underset{|}{C}}}-R'$$

| X¹ | X² | R¹ | R² | R³ | R⁴ | —CR⁵R⁶R' |
|---|---|---|---|---|---|---|
| Br | Br | H | H₂C=CH—CH₂OCH₂— | H | H | —CH—CH₂—C≡CH, phenyl |
| Cl | Cl | H | HC≡C—CH₂OCH₂— | H | H | —CH—CH₂—C≡CH, phenyl |
| Br | Br | H | HC≡C—CH₂OCH₂— | H | H | —CH—CH₂—C≡CH, phenyl |
| Cl | Cl | H | phenyl | H | H | —CH—CH₂—C≡CH, phenyl |
| Br | Br | H | phenyl | H | H | —CH—CH₂—C≡CH, phenyl |
| Cl | Cl | CH₃ | CH₃ | H | H | —CH—CH₂—C≡CH, phenyl |
| Br | Br | CH₃ | CH₃ | H | H | —CH—CH₂—C≡CH, phenyl |
| Cl | Cl | CH₃ | CH₃ | H | CH₃ | —CH—CH₂—C≡CH, phenyl |
| Br | Br | CH₃ | CH₃ | H | CH₃ | —CH—CH₂—C≡CH, phenyl |

The compounds of the formula (Ia) are new. The compounds of the formula (Ia) are prepared according to process variant (a).

Preferred possible diluents for the reaction according to process variant (b) are the solvents which have already been mentioned for process variant (a).

Preferred possible acid acceptors for the reaction according to process variant (b) are the acid acceptors which have already been mentioned for process variant (a).

The reaction temperature is kept between 0° C. and 80° C., preferably between 20° C. and 60° C., in process (b) according to the invention. The process is preferably carried out under normal pressure.

In carrying out process variant (b), 0.5 to 6 moles, preferably 1 to 4 moles, of iodine are employed per mole of the compound of the formula (Ia). The triiodoalkenyl or iodo-alkinyl derivatives of the formula (III) are worked up and isolated in the customary manner.

Formula (Ib) provides a definition of the compounds to be used as starting substances in process variant (c). In this formula, $x^1$, $X^2$, $R^1$, $R^2$, $R^3$, $R^4$, $R^5$ and $R^6$ represent those radicals which have been mentioned above in the definition of the formula (I). R'' in this formula (Ib) preferably represents $C_2$-$C_4$-iodoalkinyl.

Examples which may be mentioned of the compounds of the formula (Ib) are the iodoalkinyl derivatives of the compounds of the formula (Ia) listed in Table 3.

The compounds of the formula (Ib) are new. The compounds of the formula (Ib) are prepared according to process variant (b).

Preferred possible diluents for the reaction according to process variant (c) are the solvents which have already been mentioned for process variant (a).

The reaction temperature is kept between 0° C. and 60° C., preferably between 20° C. and 40° C., in process (c) according to the invention. The process is preferably carried out under normal pressure.

In carrying out process variant (c), 1 to 3 moles, preferably 1.1 to 2.0 moles, of halogen are preferably employed per mole of the compound of the formula (Ib). The trihalogenoalkenyl derivatives of the formula (I) are worked up and isolated in the customary manner.

Some of the new compounds are obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner. They are characterized by their refractive index.

The new cyclopropylmethyl(ene) ethers of the formula (I) display powerful synergistic actions when mixed with substances of any desired structure having an action against arthrapods, these synergistic actions enabling them to be used in agents for combating pests, for the control of animal pests.

The new cyclopropylmethyl(ene) ethers of the formula (I) preferably are combined with arthropodicides of the groups
(A) carbamic acid esters and/or
(B) carboxylic acid esters, including the naturally occurring and synthetic pyrethroids, and/or
(C) phosphorus compounds, such as phosphoric acid esters and phosphonic acid esters, including the thio and dithio compounds.

Surprisingly, the action of the new active compound combinations according to the invention against arthropods is substantially more powerful than the action of the individual components or the sum of the actions of the individual components. It is furthermore subtantially more powerful than the action of active compound combinations with the known synergist piperonyl butoxide. The cyclopropylmethyl(ene) ethers of the formula (I) according to the invention display this excellent synergistic activity not only with one class of active compound but with active compounds of the most diverse chemical groups of substances. The substances of the formula (I) according to the invention also have a very good bactericidal action and can additionally be used for combating Venturia species, such as, for example, against the apple scab causative organism (Venturia inaequalis).

The synergistic action of the compounds of the formula (I) is particularly preferably shown with
(A) Carbamic acid esters of the formula (IV)

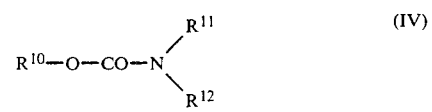

in which
$R^{10}$ represents an optionally substituted carbocyclic or heterocyclic aromatic radical or an optionally substituted oxime radical (the radicals $R^{10}$ described below being preferred),
$R^{11}$ represents $C_1$-$C_4$-alkyl and
$R^{12}$ represents hydrogen, $C_1$-$C_4$-alkyl or a radical Y wherein
Y represents the radical —CO-$R^{13}$,
wherein
$R^{13}$ represents halogen, $C_1$-$C_4$-alkyl, $C_1$-$C_4$-alkoxy, $C_3$-$C_5$-alkenoxy, $C_3$-$C_5$-alkinoxy, $C_1$-$C_4$-alkylthio, $C_1$-$C_4$-alkyl-amino, di-$C_1$-$C_4$-alkylamino or $C_1$-$C_4$-alkyl-hydroxylamino, or represents phenoxy, phenylthio or phenylamino which is optionally substituted by halogen, nitro, cyano, trifluoromethyl, $C_1$-$C_4$-alkyl, $C_1$-$C_4$-alkoxy, $C_1$-$C_4$-alkylenedioxy, $C_1$-$C_4$-alkylthio or $C_1$-$C_4$-alkoxycarbonyl, or represents 2,3-dihydro-2,2-dimethyl-7-benzofuranyl, or represents the radical

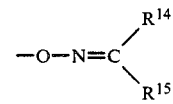

wherein
$R^{14}$ represents hydrogen, $C_1$-$C_4$-alkyl or di-$C_1$-$C_4$-alkyl-aminocarbonyl and
$R^{15}$ represents $C_1$-$C_4$-alkyl, $C_1$-$C_4$-alkylthio, cyano-$C_1$-$C_4$-alkylthio or $C_1$-$C_4$-alkylthio-$C_1$-$C_4$-alkyl, or
the two radicals $R^{14}$ and $R^{15}$ together represent $C_2$-$C_8$-alkanediyl, which is optionally interrupted by oxygen, sulphur, SO or $SO_2$, or
in which
Y represents the radical —$S_n(O)_m$-$R^{16}$,
wherein
n represents 1 or 2,
m represents 0, 1 or 2 and
$R^{16}$ represents $C_1$-$C_4$-alkyl, $C_3$-$C_5$-alkenyl, $C_3$-$C_5$-alkenyl, $C_3$-$C_5$-alkinyl or $C_3$-$C_6$-cycloalkyl which is optionally substituted by halogen, or represents phenyl, benzyl or phenethyl which is optionally substituted by halogen, cyano, nitro, trifluoromethyl, trifluoromethoxy, trifluoromethylthio, $C_1$-$C_4$-alkyl or $C_1$-$C_4$-alkoxy, or represents the radical

wherein
$R^{17}$ represents $C_1$-$C_4$-alkyl, $C_3$-$C_5$-alkenyl, $C_3$-$C_6$-cycloalkyl or benzyl and
$R^{18}$ represents $C_1$-$C_4$-alkyl, $C_3$-$C_5$-alkenyl, $C_3$-$C_5$-alkinyl, $C_3$-$C_6$-cycloalkyl, benzyl, phenethyl, halogenocarbonyl, formyl, $C_1$-$C_4$-alkylcarbonyl, $C_1$-$C_4$-alkoxy-carbonyl, $C_1$-$C_4$-alkoxyphenoxycarbonyl, $C_3$-$C_5$-alkinoxy-carbonyl, $C_3$-$C_5$-alkenyloxycarbonyl, $C_1$-$C_4$-alkylthiocarbonyl, $C_1$-$C_4$-alkylamino-carbonyl, $C_1$-$C_4$-alkyl-hydroxylamino-carbonyl, $C_1$-$C_4$-alkyl-phenoxycarbonyl, di-$C_1$-$C_4$-alkylamino-carbonyl, phenylthiocarbonyl, phenoxycarbonyl or 2,3-dihydro-2,2-dimethyl-7-benzofuranyloxycarbonyl, or represents phenylsulphenyl, phenylsulphinyl, phenylsulphonyl or phenyl which is optionally substituted by halogen, cyano, nitro, trifluoromethyl, $C_1$-$C_{10}$-alkyl or $C_1$-$C_4$-alkoxy, or represents the radical

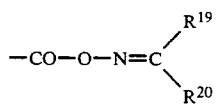

wherein
$R^{19}$ has the meaning given above for $R^{14}$ and
$R^{20}$ has the meaning given above for $R^{15}$,
and wherein, furthermore,
the radicals $R^{17}$ and $R^{18}$ in the radical

together represent a hydrocarbon chain which has 3 to 8 carbon atoms and is optionally interrupted by oxygen or sulphur,
and wherein, furthermore,
$R^{16}$ can also represent the same radical to which the radical $-S_n(O)_m$-$R^{16}$ is bonded.

Carbamic acid esters of the formula (IV) which are very particularly preferred active compound components are those
in which
$R^{10}$ represents radicals from the series comprising phenyl, naphthyl, 2,3-dihydro-7-benzofuranyl, pyrazolyl and pyrimidinyl which are optionally substituted by $C_1$-$C_4$-alkyl, $C_2$-$C_4$-alkenyl, $C_1$-$C_4$-alkoxy, $C_1$-$C_4$-alkoxy-methyl, $C_1$-$C_4$-alkylthio, $C_1$-$C_4$-alkylthio-methyl, $C_1$-$C_4$-alkylamino, di-($C_1$-$C_4$-alkyl)-amino, di-($C_3$-$C_4$-alkenyl)amino, halogen, dioxolanyl, methylenedioxy, dimethyl-methylenedioxy, and/or by the radical $-N=CH(CH_3)_2$,
or in which
$R^{10}$ represent an alkylideneamino radical of the formula (Iva)

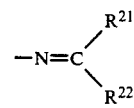

in which
$R^{21}$ and $R^{22}$ have the meaning given above for $R^{14}$ and $R^{15}$ respectively, and
$R^{11}$ represents $C_1$-$C_4$-alkyl and
$R^{12}$ represents hydrogen or $C_1$-$C_4$-alkyl (preferably hydrogen).

Examples which may be mentioned of the carbamic acid esters of the formula (IV) are: 2-methyl-phenyl-, 2-ethyl-phenyl, 2-iso-propyl-phenyl, 2-sec-butyl-phenyl-, 2-methoxy-phenyl-, 2-ethoxy-phenyl-, 2-iso-propoxy-phenyl-, 4-methyl-phenyl-, 4-ethyl-phenyl-, 4-n-propyl-phenyl-, 4-methoxy-phenyl-, 4-ethoxy-phenyl-, 4-n-propoxy-phenyl-, 3,4,5-trimethyl-phenyl-, 3,5-dimethyl-4-methylthio-phenyl-, 3-methyl-4-dimethylaminophenyl-, 2-ethyl-thiomethylphenyl-, 1-naphtyl-, 2,3-dihydro-2,2-dimethyl-7-benzofuranyl, 2,3-(dimethyl-methylene-dioxy)-phenyl-, 2-(1,3-dioxolan-2-yl)-phenyl-, 2-(4,5-dimethyl-1,3-dioxolan-2-yl)-phenyl-, 1-methylthio-ethylidene-amino-, 2-methylthio2-methyl-propylideneamino, 1-(2-cyano-ethylthio)-ethylideneamino- and 1-methylthiomethyl-2,2-dimethyl-propylideneamino-N-methyl-carbamic acid ester.

The synergistic action of the compounds of the formula (I) is also preferably displayed with:
(B) carboxylic acid esters of the formula (V)

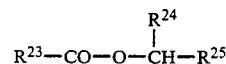

in which
$R^{23}$ represents and open-chain or cyclic alkyl radical, which is optionally substituted by halogen, alkyl or cycloalkyl, by alkenyl which is optionally substituted by halogen, alkyl and/or alkoxy, by phenyl or styryl which is optionally substituted by halogen or optionally halogen-substituted radicals from the series comprising alkyl, alkoxy, alkylenedioxy and/or alkylthio, or by optionally halogen-substituted cycloalk(en)yl, which is linked in a spirocyclic manner and is optionally benzo-fused,
and in which, furthemore,
$R^{24}$ represents hydrogen, alkyl, halogenoalkyl, alkenyl, alkinyl or cyano and
$R^{25}$ represents an optionally substituted alkyl or aryl radical or a heterocyclic radical, or, together with $R^{24}$ and the carbon atom to which the two radicals are bonded, forms a cyclopentenone ring.

Carboxylic acid esters of the formula (V) which are very particularly preferred active compound combinations are those
in which
$R^{23}$ represents the radical

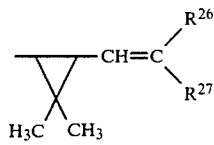

wherein
$R^{26}$ represents hydrogen, methyl, fluorine, chloride or bromine and $R^{27}$ represents methyl, fluorine, chlorine, bromine, $C_1$–$C_2$-fluoroalkyl or $C_1$–$C_2$-chlorofluoroalkyl, or represents phenyl which is optionally substituted by halogen and/or optionally halogen-substituted radicals from the series comprising $C_1$–$C_4$-alkyl, $C_1$–$C_4$-alkoxy, $C_1$–$C_4$-alkylthio and/or $C_1$–$C_2$-alkylenedioxy, or wherein the two radicals $R^{26}$ and $R^{27}$ represent $C_2$–$C_5$-alkanediyl (alkylene);

or in which $R^{23}$ represents the radical

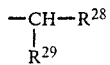

wherein $R^{28}$ represents phenyl which is optionally substituted by halogen and/or by optionally halogen-substituted radicals from the series comprising $C_1$–$C_4$-alkyl, $C_1$–$C_4$-alkoxy, $C_1$–$C_4$-alkylthio and $C_1$–$C_2$-alkylenedioxy and $R^{29}$ represents isopropyl or cyclopropyl; on in which $R^{23}$ represents one of the radicals

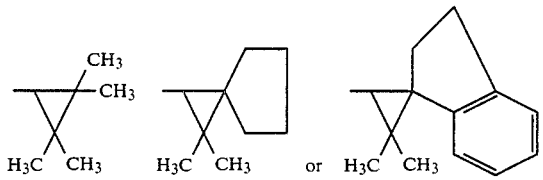

wherein
the dotted lines are intended to indicate possible double bonds, or $R^{23}$ represents methyl, and in which, furthermore, $R^{24}$ represents hydrogen, $C_1$–$C_4$-alkyl, $C_1$–$C_4$-halogenoalkyl, cyano or ethinyl and $R^{25}$ represents optionally halogen-substituted radicals of the series comprising phenyl, furyl and tetrahydophthalimido, it being possible for these radicals to be further substituted by optionally by halogen and/or by an optionally halogen-substituted radical from the series comprising $C_1$–$C_4$-alkyl, $C_2$–$C_4$-alkenyl, $C_1$–$C_4$-alkoxy, $C_2$–$C_4$-alkenoxy, $C_1$–$C_4$-alkylthio, $C_1$–$C_2$-alkyl-lenedioxy, phenoxy and/or benzyl, and wherein, preferably, $R^{25}$ represents pentafluorophenyl, benzylfuryl, phenoxyphenyl, which can be substituted by halogen in one or both phenyl rings, 3,4-dichlorophenyl or tetrahydrophthalimido.

The naturally occurring pyrethroids (such as pyrethrum) are also particularly preferred as carboxylic acid esters of the formula (V).

Examples which may be mentioned of the carboxylic acid esters of the formula (V) are: 2,2,2-trichloro-1-(3,4)dichloro-phenyl)-ethyl acetate, 3,4,5,6-tetrahydrophthalimido-methyl 2,2-dimethyl-3-(2-methyl-propen-1-yl)-cyclopropane-carboxylate, 3-phenoxy-benzyl 2,2-dimethyl-3-(2,2-dichlorovinyl)-cyclopropane-carboxylate, α-cyano-3-phenoxy-benzyl 2,2-dimethyl-3-(2,2-dichlorovinyl)-cyclopropane-carboxylate, α-cyano-4-fluoro-3-phenoxy-benzyl 2,2-dimethyl-3-(2,2-dichlorovinyl)-cyclopropane-carboxylate, pentafluorobenzyl 2,2-dimethyl-3-(2,2-dichlorovinyl)-cyclopropane-carboxylate, α-cyano-3-phenoxy-benzyl 2,2-dimethyl-3-(2,2-dibromovinyl)-cyclopropane-carboxylate, α-cyano-3-phenoxy-benzyl 3-methyl-2-(4-chlorophenyl)-butanoate and 5-benzyl-3-furyl-methyl 2,2-dimethyl-3-(2-methylpropen-1-yl)-cyclopropane-carboxylate.

The synergistic action of the compounds of the general formula (I) is also preferably displayed with (C) phosphoric acid esters and phosphonic acid esters of the general formula (VI)

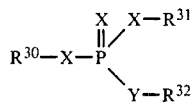

in which

X in each case represents O or S,

Y represents O, S, —NH— or a direct bond between the central P atom and $R^{32}$, $R^{30}$ and $R^{31}$ are identical or different and represent optionally substituted alkyl or aryl and $R^{32}$ represents hydrogen, optionally substituted alkyl, aryl, heteroaryl, aralkyl, alkenyl, dioxanyl or an oxime radical or the same radical to which it is bonded.

Particularly preferred phosphoric acid esters and phosphonic acid esters of the formula (VI) are those in which $R^{30}$ and $R^{31}$ are identical or different and represent $C_1$–$C_4$-alkyl or phenyl and $R^{32}$ represents hydrogen, alkyl which has 1 to 4 carbon atoms and is optionally substituted by halogen, hydroxyl, cyano, optionally halogen-substituted phenyl, carbamoyl, alkylsulphonyl, alkylsulphinyl, alkylcarbonyl, alkoxy, alkylmercapto, alkoxycarbonyl or alkylaminocarbonyl, the latter with in each case up to 6 carbon atoms, or represents alkenyl which has up to 4 carbon atoms and is optionally substituted by halogen, optionally halogen-substituted phenyl or $C_1$–$C_4$-alkoxycarbonyl, or represents the radical of the general formula (VIa)

wherein $R^{33}$ and $R^{34}$ have the meaning given above for $R^{14}$ and $R^{15}$ respectively, or represent cyano or phenyl and in which $R^{32}$ furthermore represents dioxanyl, which is substituted by the same radical to which $R^{32}$ is bonded, or $R^{32}$ represents the same radical to which it is bonded, or $R^{32}$ represents phenyl which is optionally substituted by methyl, nitro, cyano, halogen and/or methylthio, or $R^{32}$ also particularly preferably represents optionally by $C_1$–$C_4$-alkoxy, $C_1$–$C_4$-alkylthiomethyl, $C_1$–$C_4$-alkyl and/or halogen-substituted heteroaromatic radicals, such as pyridinyl, quinolinyl, quinoxalinyl, pyrimidinyl or benzo-1,2,4-triazinyl.

Compounds which may be mentioned specifically are: O,O-dimethyl or O.O-diethyl O-(2,2-dichloro- or 2,2-dibromovinyl) phosphate, O,O-diethyl O-(4-nitrophenyl) thionophosphate, O,O-dimethyl O-(3-methyl-4-methylthio-phenyl) thionophosphate, O,O-dimethyl O-(3-methyl-4-nitro-phenyl) thionophosphate, O-ethyl S-n-propyl O-(2,4-dichlorophenyl) thionophosphate, O-ethyl S-n-propyl O-(4-methylthio-phenyl) thionophosphate, O,O-dimethyl S-(4-oxo-1,2,3-benzotriazin-3-yl-methyl) thionothiolphosphate, O-methyl O-(2-isopropyl-6-methoxy-pyrimidin-4-yl)thionomethanephosphate, O,O-diethyl O-(2-iso-propyl-6-methyl-pyrimidin-4-yl) thionophosphate, O,O-diethyl O-(3-chloro-4-methyl-coumarin-7-yl) thionophosphate, O,O-dimethyl 2,2,2-trichloro-1-hydroxy-ethane-phosphonate and O,O-dimethyl S-(methylaminocarbonyl-methyl) thionophosphate.

The weight ratios of the synergists and active compounds can be varied within a relatively wide range. In general, the compounds of the formula (I) used as synergists are used with the other active compounds in mixing ratios of between 1:100 and 100:1, preferably between 1:5 and 5:1 (parts by weight).

The active compound combinations according to the invention have not only a rapid knock-down action but also effect long-lasting destruction of the animal pests, in particular insects and mites which occur in agriculture, in forestry, in the protection of stored products and of materials and in the hygiene sector. They are effective against normally sensitive and resistant species and against all or some stages of development.

The animal pests which can be combated using the compounds of the formula (I) include, for example:

From the order of the Isopoda, for example, *Oniscus asellus* and *Porcellio scaber*. From the order of the Thysanura, for example *Lepisma saccharina*. From the order of the Orthoptera, for example, *Blatta orientalis, Periplaneta americana, Leucophaea maderae, Blattella germanica, Acheta domesticus,* Gryllotalpa spp., *Locusta migratoria migratorioides* and *Schistocerca gregaria*. From the order of the Dermaptera, for example, *Forficula auricularia*. From the order of the Isoptera, for example, Reticulitermes spp.. From the order of the Anoplura, for example, *Pediculus humanus corporis,* Haematopinus spp. and Linograthus spp. From the order of the Mallophaga, for example, Trichodectes spp. and Damalinea spp. From the order of the Heteroptera, for example, *Cimex lectularius, Rhodnius prolixus* and Triatoma spp. From the order of the Homoptera, for example, Myzus spp. and Psylla spp. From the order of the Lepidoptera, for example, *Ephestia kuehniella* and *Galleria mellonella*. From the order of the Coleoptera, for example, *Anobium punctatum, Rhizopertha dominica, Bruchidus obtectus, Acanthoscelides obtectus, Hylotrupes bajulus, Oryzaephilus surinamensis,* Sitophilus spp. Dermestes spp., Trogoderma spp., Anthrenus spp., Attagenus spp., Lyctus spp., Ptinus spp., *Niptus hololeucus,* Gibbium psylloides, Tribolium spp. and *Tenebrio molitor*. From the order of the Hymenoptera, for example, Lasius spp., Monomorium pharaonis and Vespa spp. From the order of the Diptera, for example, *Aedes spp., Anopheles spp., Culex spp., Drosophila melanogaster,* Musca spp., Fannia spp., Calliphora erythrocephala, Lucilia spp., Chrysomyia spp., Gastrophilus spp., Hyppobosca spp., Stomoxys spp., Oestrus spp., Hypoderma spp. and Tabanus spp. From the order of the Siphonaptera, for example, *Xenopsylla cheopis* and Ceratophyllus spp.. From the order of the Arachnida, for example, *Scorpio maurus* and *Latrodectus mactans*. From the order of the Acarina, for example, *Acarus siro,* Argas spp., Ornithodoros spp., Dermanyssus gallinae, Boophilus spp., Rhipicephalus spp., Amblyomma spp., Hyalomma spp., Ixodes spp., Psoroptes spp., Chorioptes spp. and Sarcoptes spp.

The active compound combinations of the compounds of the formula (I) and the other active compounds can be converted to the customary formulations, such as solutions, emulsions, wettable powders, suspensions, powders, dusting agents, foams, pastes, soluble powders, aerosols, suspension-emulsion concentrates, natural and synthetic materials impregnated with active compound, very fine capsules in polymeric substances, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that it liquid solvents, liquefied gases under pressure, and/or solid carriers, optionally with the use of surface-active agents, that is, emulsifying agents and/or dispersing agents, and/or foam-forming agents.

In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: non-ionic and anionic emulsifiers, such as polyoxyethylene-fatty acid esters, polyoxyethylene-fatty alcohol ethers, for example alkylaryl polyglycol ethers and alkyl sulphonates; as dispersing agents there are suitable: for example lignin, sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound combination, preferably between 0.5 and 90%.

The active compound combinations according to the invention are used in the form of their commercially available formulations and/or the use forms prepared from these formulations.

The total content of active compound (including synergist) of the use forms prepared from the commercially available formulations can be varied within wide limits. The active compound concentration of the use form can be from 0.0001 to 100% by weight of active compound combination, preferably between 0.01 and 10% by weight.

The combinations are employed in a customary manner appropriate for the use forms.

When used against products, compound combinations are distinguished by an outstanding residual action on wood and clay as well as by a good stability to alkali on limed substrates.

The activity of the compounds of the formula (I) which can be used according to the invention is illustrated with the aid of the following examples:

I. Examples of active compounds which can be used according to the invention

| Formula | Common name: |
|---|---|
| (A.) [structure with O-C(=O)-NHCH$_3$ and OC$_3$H$_7i$ on benzene ring] | (propoxur) |
| (B.) [benzofuran structure with CH$_3$, CH$_3$ and O-CNHCH$_3$ group] | (carbofuran) |
| (C.) [benzene ring with O-C(=O)-NHCH$_3$ and dioxolane with two CH$_3$] | (bendiocarb) |
| (D.) [benzene ring with O-C(=O)-NHCH$_3$ and dioxolane] | (dioxocarb) |
| (E.) CH$_3$—HN—C(=O)—O—N=C(CH$_3$)—S—CH$_3$ | (mathomyl) |
| (F.) Pyrethrins of natural origin as a 25% strength extract | |
| (G.) (CH$_3$)$_2$C=CH—[cyclopropane with CH$_3$ CH$_3$]—C(=O)—O—CH$_2$—N[cyclohexene dicarboximide] | (tetramethrin) |

| Formula | Common name: |
|---|---|
| (H.) Cl₂C=CH-[cyclopropane(CH₃,CH₃)]-C(=O)-O-CH₂-C₆H₄-O-C₆H₅ | (permethrin) |
| (I.) Br₂C=CH-[cyclopropane(CH₃,CH₃)]-C(=O)-O-CH(CN)-C₆H₄-O-C₆H₅ | (decamethrin) |
| (J.) (CH₃)₂C=CH-[cyclopropane(CH₃,CH₃)]-C(=O)-O-CH₂-(furan)-CH₂-C₆H₅ | (resmethrin) |
| (K.) Cl₂C=CH-[cyclopropane(CH₃,CH₃)]-C(=O)-O-CH₂-C₆F₄ | |
| (L.) Cl₂C=CH-[cyclopropane(CH₃,CH₃)]-C(=O)-O-CH(CN)-C₆H₃(F)-O-C₆H₅ | |
| (M.) 3,4-Cl₂-C₆H₃-CH(CCl₃)-O-C(=O)-CH₃ | (penfenate) |
| (N.) Cl₂C=CH-O-P(=O)(OCH₃)₂ | (DDVP) |
| (O.) (CH₃O)₂P(=O)-S-CH₂-C(=O)-N(CH₃)H | (omethoat) |

II. Examples of synergists which can be used according to the invention

| No. | Formula |
|---|---|
| 1. | [Cyclopropane with 2 Cl on one C]-CH₂OCH₂-C≡CH |
| 2. | [Cyclopropane with 2 Cl on one C, CH₃ on another]-CH₂OCH₂-C≡CH |
| 3. | [Cyclopropane with 2 Cl on one C, CH₃ on another]-CH₂-O-CH₂-C≡CH |
| 4. | [Cyclopropane with 2 Br on one C]-CH₂OCH₂-C≡CH |
| 5. | [Cyclopropane with 2 Br on one C, CH₃ on another]-CH₂OCH₂-C≡CH |
| 6. | [Cyclopropane with 2 Br on one C]-CH₂OCH₂-C≡CCl |

-continued

| No. | Formula |
|---|---|
| 7. | H₃C–C(Br)(Br)–CH₂OCH₂–C≡CI |
| 8. | H₃C–C(Cl)(Cl)–CH₂OCH₂–C≡CI |
| 9. | (Cl)(Cl)C–C(CH₃)–CH₂OCH₂–C≡CI |
| 10. | BrCH₂–C(Cl)(Cl)–CH₂OCH₂–C≡CI |
| 11. | BrCH₂–C(Cl)(Cl)–CH₂OCH₂–C≡CH |
| 12. | IC≡C–CH₂–O–CH₂–C(Cl)(Cl)–CH₂–O–CH₂–C≡CI |
| 13. | HC≡C–CH₂–O–CH₂–C(Cl)(Cl)–CH₂–O–CH₂–C≡CH |
| 14. | CH₃–C(Br)(Br)–CH₂–O–CH₂CI≡CI₂ |

Comparison compound: piperonyl butoxide (known)
15. [structure]

III. Test procedure

| LT₁₀₀ test | |
|---|---|
| Test insects: | female *Musca domestica* (Weymanns strain) resistant to phosphates and carbamates |
| Solvent: | acetone |

Solutions of the active compounds, synergists and mixtures of active compounds and synergists are prepared, and 2.5 ml thereof are pipetted onto filter paper discs 9.5 cm in diameter in Petri dishes. The filter paper absorbs the solution. The Petri dishes remain uncovered until the solvent has evaporated completely. 25 test insects are then introduced into the Petri dishes and the dishes are covered with a glass lid.

The condition of the test insects is monitored continuously for up to 6 hours. The time required for a 100% knock-down effect is determined. If the LT₁₀₀ has not been reached after 6 hours, the percentage of knocked-down test insects is determined.

The concentrations of the active compounds, synergists and mixtures and their actions can be seen from the following table. The experiments were carried out in 2 experimental series (1 and 2) in direct comparison experiments. Certain differences in action thus resulted with some active compounds (without admixed synergist).

IV. Test results $LT_{100}$ test with female *Musca domestica* (Weymanns strain) resistant to phosphates and carbamates.

| | Experimental series 1: | | |
|---|---|---|---|
| Active compound/ synergist | | Concentration in % active compound/ synergist | $LT_{100}$ in or at 360' in % |
| A | | 1.0 | 360' = 20% |
| B | | 1.0 | 360' = 25% |
| C | | 1.0 | 360' = 0% |
| E | | 0.2 | 360' = 95% |
| F | | 0.2 | 150' |
| G | | 0.2 | 180' |
| H | | 0.04 | 360' |
| I | | 0.008 | 90' |
| J | | 0.04 | 240' |
| M | | 1.0 | 360' = 80% |
| N | | 0.008 | 360' = 95% |
| 1 | | 1.0 | 360' = 40% |
| 2 | | 1.0 | 360' = 0% |
| 3 | | 1.0 | 360' = 5% |
| 4 | | 1.0 | 360' = 40% |
| 5 | | 1.0 | 360' = 50% |
| 15 (known) | | 1.0 | 360' = 0% |
| A | +15 | 1.0  +1.0 | 240' |
| A | +1 | 0.04  +0.04 | 150' |
| A | +2 | 0.04  +0.04 | 90' |
| A | +3 | 0.04  +0.04 | 105' |
| A | +4 | 0.04  +0.04 | 90' |
| A | +5 | 0.04  +0.04 | 105' |
| B | +15 | 0.04  +0.04 | 360' = 50% |
| B | +1 | 0.04  +0.04 | 210' |
| B | +2 | 0.04  +0.04 | 180' |
| B | +4 | 0.04  +0.04 | 180' |
| B | +5 | 0.04  +0.04 | 120' |
| C | +15 | 0.2  +0.2 | 360' = 80% |
| C | +1 | 0.04  +0.04 | 150' |
| C | +2 | 0.04  +0.04 | 150' |
| C | +3 | 0.04  +0.04 | 150' |
| C | +4 | 0.04  +0.04 | 180' |
| C | +5 | 0.04  +0.04 | 150' |
| E | +15 | 0.04  +0.04 | 360' = 30% |
| E | +1 | 0.04  +0.04 | 150' |
| E | +2 | 0.04  +0.04 | 180' |
| E | +3 | 0.04  +0.04 | 105' |
| E | +4 | 0.04  +0.04 | 150' |
| E | +5 | 0.04  +0.04 | 150' |
| F | +2 | 0.2  +0.2 | 75' |
| F | +4 | 0.2  +0.2 | 75' |
| F | +5 | 0.2  +0.2 | 75' |
| G | +1 | 0.2  +0.2 | 120' |
| G | +2 | 0.2  +0.2 | 105' |
| G | +4 | 0.2  +0.2 | 90' |
| G | +5 | 0.2  +0.2 | 60' |
| H | +15 | 0.04  +0.04 | 120' |
| H | +1 | 0.04  +0.04 | 105' |
| H | +2 | 0.04  +0.04 | 90' |
| H | +4 | 0.04  +0.04 | 60' |
| H | +5 | 0.04  +0.04 | 105' |
| I | +1 | 0.008  +0.008 | 60' |
| I | +2 | 0.008  +0.008 | 60' |
| I | +4 | 0.008  +0.008 | 60' |
| I | +5 | 0.008  +0.008 | 60' |
| J | +1 | 0.04  +0.04 | 150' |
| J | +2 | 0.04  +0.04 | 150' |
| J | +4 | 0.04  +0.04 | 120' |
| J | +5 | 0.04  +0.04 | 105' |
| M | +15 | 1.0  +1.0 | 360' = 95% |
| M | +1 | 1.0  +1.0 | 210' |
| M | +2 | 0.2  +0.2 | 210' |
| M | +3 | 0.2  +0.2 | 210' |

-continued

Experimental series 1:

| Active compound/ synergist | | Concentration in % active compound/ synergist | | $LT_{100}$ in or at 360' in % |
|---|---|---|---|---|
| M | +4 | 0.2 | +0.2 | 150' |
| M | +5 | 0.2 | +0.2 | 180' |
| N | +15 | 0.008 | +0.008 | 90' |
| N | +1 | 0.008 | +0.008 | 75' |
| N | +2 | 0.008 | +0.008 | 90' |
| N | +3 | 0.008 | +0.008 | 75' |
| N | +4 | 0.008 | +0.008 | 75' |
| N | +5 | 0.008 | +0.008 | 75' |

Experimental series 2:

| Active compound/ synergist | | Concentration in % active compound/ synergist | | $LT_{100}$ in or at 360' in 5% |
|---|---|---|---|---|
| A | | 1.0 | | 360' = 5% |
| B | | 0.2 | | 360' = 40% |
| C | | 1.0 | | 360' = 0% |
| D | | 1.0 | | 360' = 0% |
| E | | 0.2 | | 360' = 30% |
| F | | 0.04 | | 360' = 20% |
| G | | 0.04 | | 360' = 50% |
| H | | 0.008 | | 210' |
| L | | 0.0016 | | 360' = 95% |
| M | | 0.04 | | 360' = 30% |
| N | | 0.04 | | 90' |
| O | | 0.04 | | 360' = 10% |
| | 6 | 1.0 | | 360' = 0% |
| | 7 | 1.0 | | 360' = 30% |
| | 8 | 0.2 | | 360' = 40% |
| | 9 | 0.2 | | 360' = 80% |
| | 10 | 1.0 | | 360' = 0% |
| | 11 | 0.2 | | 360' = 0% |
| | 12 | 1.0 | | 360' = 0% |
| | 13 | 1.0 | | 360' = 30% |
| | 14 | 1.0 | | 360' = 0% |
| | 15 (known) | 1.0 | | 360' = 0% |
| A | +6 | 0.2 | +0.2 | 105' |
| A | +7 | 0.04 | +0.04 | 240' |
| A | +8 | 0.04 | +0.04 | 150' |
| A | +9 | 0.04 | +0.04 | 120' |
| A | +10 | 0.2 | +0.2 | 360' |
| A | +11 | 0.2 | +0.2 | 120' |
| A | +12 | 0.2 | +0.2 | 360' = 90% |
| A | +13 | 0.04 | +0.04 | 210' |
| A | +15 | 0.2 | +0.2 | 360' = 45% |
| B | +6 | 0.04 | +0.04 | 150' |
| B | +7 | 0.2 | +0.2 | 150' |
| B | +8 | 0.04 | +0.04 | 150' |
| B | +9 | 0.04 | +0.04 | 105' |
| B | +10 | 0.2 | +0.2 | 360' = 80% |
| B | +11 | 0.04 | +0.04 | 180' |
| B | +12 | 0.2 | +0.2 | 360' |
| B | +13 | 0.04 | +0.04 | 180' |
| B | +15 | 0.2 | +0.2 | 360' = 40% |
| C | +6 | 0.2 | +0.2 | 150' |
| C | +7 | 0.2 | +0.2 | 360' |
| C | +8 | 0.2 | +0.2 | 120' |
| C | +9 | 0.04 | +0.04 | 150' |
| C | +11 | 0.2 | +0.2 | 240' |
| C | +13 | 0.2 | +0.2 | 150' |
| C | +15 | 0.2 | +0.2 | 360' = 40% |
| D | +6 | 0.2 | +0.2 | 240' |
| D | +7 | 0.2 | +0.2 | 360' = 90% |
| D | +8 | 0.2 | +0.2 | 240' |
| D | +9 | 0.2 | +0.2 | 210' |
| D | +11 | 0.2 | +0.2 | 360' |
| D | +13 | 0.2 | +0.2 | 360' |
| D | +15 | 0.2 | +0.2 | 360' = 20% |
| E | +6 | 0.2 | +0.2 | 180' |
| E | +7 | 0.2 | +0.2 | 180' |
| E | +8 | 0.2 | +0.2 | 150' |
| E | +9 | 0.2 | +0.2 | 105' |
| E | +10 | 0.2 | +0.2 | 360' = 90% |
| E | +11 | 0.2 | +0.2 | 120' |
| E | +12 | 0.2 | +0.2 | 210' |

Experimental series 2:

| Active compound/ synergist | | Concentration in % active compound/ synergist | | $LT_{100}$ in or at 360' in 5% |
|---|---|---|---|---|
| E | +13 | 0.2 | +0.2 | 150' |
| E | +14 | 0.2 | +0.2 | 210' |
| F | +6 | 0.04 | +0.04 | 180' |
| F | +7 | 0.04 | +0.04 | 240' |
| F | +8 | 0.04 | +0.04 | 180' |
| F | +9 | 0.04 | +0.04 | 180' |
| F | +11 | 0.04 | +0.04 | 180' |
| F | +13 | 0.04 | +0.04 | 150' |
| G | +6 | 0.04 | +0.04 | 90' |
| G | +7 | 0.04 | +0.04 | 210' |
| G | +8 | 0.04 | +0.04 | 90' |
| G | +9 | 0.04 | +0.04 | 90' |
| G | +10 | 0.04 | +0.04 | 210' |
| G | +11 | 0.04 | +0.04 | 105' |
| G | +12 | 0.04 | +0.04 | 180' |
| G | +13 | 0.04 | +0.04 | 90' |
| G | +14 | 0.04 | +0.04 | 210' |
| H | +6 | 0.008 | +0.008 | 90' |
| H | +8 | 0.008 | +0.008 | 105' |
| H | +9 | 0.008 | +0.008 | 105' |
| H | +13 | 0.008 | +0.008 | 105' |
| H | +15 | 0.008 | +0.008 | 150' |
| L | +6 | 0.0016 | +0.0016 | 120' |
| L | +7 | 0.0016 | +0.0016 | 120' |
| L | +8 | 0.0016 | +0.0016 | 120' |
| L | +9 | 0.0016 | +0.0016 | 150' |
| L | +10 | 0.0016 | +0.0016 | 210' |
| L | +11 | 0.0016 | +0.0016 | 120' |
| L | +12 | 0.0016 | +0.0016 | 105' |
| L | +13 | 0.0016 | +0.0016 | 105' |
| L | +14 | 0.0016 | +0.0016 | 105' |
| M | +6 | 0.04 | +0.04 | 240' |
| M | +8 | 0.04 | +0.04 | 210' |
| M | +9 | 0.04 | +0.04 | 240' |
| M | +15 | 0.04 | +0.04 | 360' = 80% |
| N | +7 | 0.04 | +0.04 | 75' |
| N | +9 | 0.04 | +0.04 | 45' |
| N | +10 | 0.04 | +0.04 | 60' |
| N | +11 | 0.04 | +0.04 | 60' |
| N | +12 | 0.04 | +0.04 | 75' |
| N | +14 | 0.04 | +0.04 | 75' |
| O | +6 | 0.04 | +0.04 | 360' |
| O | +7 | 0.04 | +0.04 | 360' |
| O | +8 | 0.04 | +0.04 | 240' |
| O | +9 | 0.04 | +0.04 | 150' |
| O | +10 | 0.04 | +0.04 | 360' |
| O | +11 | 0.04 | +0.04 | 360' |
| O | +13 | 0.04 | +0.04 | 240' |

The preparation of the compounds of the formula (I) is illustrated with the aid of the following preparation examples (unless indicated otherwise, all per cent data relate to percentages by weight):

Example 1

(PROCESS VARIANT A) Synergist No. 1

3 g of sodium hydride (80% in liquid paraffin) are added in small portions to 100 ml of propargyl alcohol which has been cooled to 0° C; during the addition, the temperature is kept at 0° to 5° C. The mixture is stirred at this temperature for a further 10 minutes and 21 g (0.1 mole) of 1,1-dichloro-2-bromomethylcyclopropane are then added dropwise at 0° C. in the course of 10 minutes. The mixture is heated at 70° C. for 14 hours and cooled to about 20° C. After the solid residue has been filtered off with suction, it is rinsed with 200 ml of methylene chloride. The organic phase is freed from the solvent and from excess propargyl alcohol under a water-pump vacuum at a flask temperature of 80° C. The residue is taken up in 200 ml of methylene chloride and washed with 50 ml of water. The aqueous phase is extracted again with 100 ml of methylene chloride. The combined organic phases are evaporated and the residue is then rectified.

7.8 g (43% of theory) of 3-(2,2-dichlorocyclopropylmethoxy)-1-propine of refractive index $n_D^{20}$ 1.4850 are obtained.

EXAMPLE 2

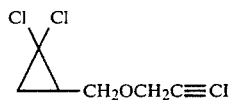

(PROCESS VARIANT B)

4.5 g (0.025 mole) of 3-(2,2-dichlorocyclopropylmethoxy)-1-propine are dissolved in 100 ml of methanol, and 6.3 g (0.025 mole) of iodine and 2.5 g of 45% strength sodium hydroxide solution are added in alternating portions at 20° C. After the addition, the mixture is stirred at 20° C. for a further hour. After the methanol has been distilled off, the residue is taken up in 100 ml of methylene chloride and the mixture is washed with 50 ml of dilute sodium thiosulphate solution and then with 50 ml of water. The organic phase is dried over magnesium sulphate.

After incipient distillation under 1 mbar (100 Pa) and at 95° C., 3.8 g (50% of theory) of 3-(2,2-dichlorocyclopropylmethoxy)-1-iodo-1-propine of refractive index $n_D^{20}$ 1.5818 are obtained.

EXAMPLE 3

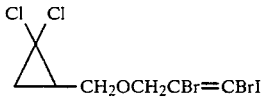

(PROCESS VARIANT C)

3 g (0.01 mole) of 3-(2,2-dichlorocyclopropylmethoxy)-1-iodo-1-propine are dissolved in 50 ml of methylene chloride, and 2 g (0.0125 mole) of bromine in 20 ml of methylene chloride are added at 20° C. The mixture is then stirred at 60° C. for 14 hours. After cooling to 20° C., the mixture is washed with 20 ml of aqueous sodium thiosulphate solution and then with water. The organic phase is dried over magnesium sulphate and the solvent is removed under a waterpump vacuum.

4.2 g (90% of theory) of 1,2-dibromo-3-(2,2-dichlorocyclopropylmethoxy)-iodo-1-propene of refractive index $n_D^{20}$ 1.6014 are obtained.

EXAMPLE 4

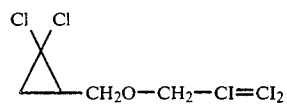

(PROCESS VARIANT B)

96 g (0.378 mole) of iodine and 13 g of 45% strength sodium hydroxide solution are added in alternating portions to 23 g (0.128 mole) of 3-(2,2-dichlorocyclopropylmethoxy)-1-propine in 100 ml of methanol at 20° C., while stirring and the mixture is stirred for 14 hours. The solvent is then distilled off under a waterpump vacuum and 500 ml of methylene chloride are added to the residue. The mixture is washed first with 200 ml of sodium thiosulphate solution and then with 200 ml of water, until it is decolorized. The organic phase is dried over magnesium sulphate and concentrated under a waterpump vacuum.

46 g (64% of theory) of 3-(2,2-dichlorocyclopropylmethoxy)-1,1,2-triiodo-1-propene of refractive index $n_D^{20}$ 1.6623 are obtained.

The compounds of the formula (I) listed in Table 4 which follows can be prepared analogously to the process variants (a), (b) or (c):

TABLE 4

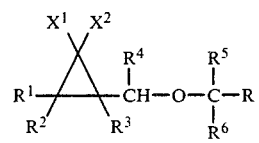

| Example No. | $X^1$ | $X^2$ | $R^1$ | $R^2$ | $R^3$ | $R^4$ | $R^5$ | $R^6$ | R | Synergist No. | Refractive index $n_D^{20}$ |
|---|---|---|---|---|---|---|---|---|---|---|---|
| 5 | Br | Br | H | CH$_3$ | H | H | H | H | —C≡CH | 5 | 1.5300 |
| 6 | Cl | Cl | H | CH$_3$ | H | H | H | H | —C≡CH | 2 | 1.4826 |
| 7 | Br | Br | H | H | H | H | H | H | —C≡CH | 4 | 1.5358 |
| 8 | Br | Br | H | H | H | H | H | H | —C≡Cl | 6 | 1.5980 |
| 9 | Cl | Cl | H | CH$_3$ | H | H | H | H | —C≡Cl | 8 | 1.5540 |
| 10 | Cl | Cl | H | H | CH$_3$ | H | H | H | —C≡Cl | 9 | 1.5530 |
| 11 | Br | Br | H | CH$_3$ | H | H | H | H | —C≡Cl | 7 | 1.5620 |
| 12 | Cl | Cl | H | H | CH$_3$ | H | H | H | —C≡CH | 3 | 1.4952 |
| 13 | Cl | Cl | H | CH$_3$ | H | H | H | H | —C=Cl<br>\|  \|<br>Cl  Cl | | 1.5484 |

TABLE 4-continued

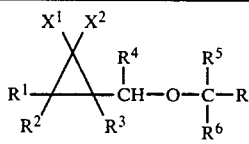

| Example No. | $X^1$ | $X^2$ | $R^1$ | $R^2$ | $R^3$ | $R^4$ | $R^5$ | $R^6$ | R | Synergist No. | Refractive index $n_D^{20}$ |
|---|---|---|---|---|---|---|---|---|---|---|---|
| 14 | Br | Br | H | CH$_3$ | H | H | H | H | −C(Cl)=CCl$_2$ | | 1.5780 |
| 15 | Br | Br | H | CH$_3$ | H | H | H | H | −CI=CI$_2$ | 14 | 1.6496 |
| 16 | Cl | Cl | H | CH$_3$ | H | H | H | H | −CBr=CBrI | | 1.5920 |
| 17 | Cl | Cl | H | CH$_3$ | H | H | H | H | −CI=CI$_2$ | | 1.6396 |
| 18 | Cl | Cl | H | −CH$_2$Br | H | H | H | H | −C≡CH | 11 | 1.5125 |
| 19 | Cl | Cl | H | −CH$_2$OCH$_2$C≡CH | H | H | H | H | −C≡CH | 13 | 1.5075 |
| 20 | Cl | Cl | H | −CH$_2$Br | H | H | H | H | −C≡CI | 10 | 1.5565 |
| 21 | Cl.Cl | | H | −CH$_2$OCH$_2$C≡CI | H | H | H | H | −C≡CI | 12 | 1.5920 |
| 22 | Cl | Cl | H | H | CH$_3$ | H | H | H | −CBr=CBrI | | 1.5391 |
| 23 | Cl | Cl | H | H | CH$_3$ | H | H | H | −CI=CI$_2$ | | 1.6464 |
| 24 | Cl | Cl | H | H | −CH$_2$Cl | H | H | H | −C≡CH | | 1.4962 |
| 25 | Cl | Cl | H | H | CH$_3$ | H | H | H | −C(Cl)=CCl | | 1.5547 |

The preparation of compounds of the formula (II) is illustrated with the aid of the following examples:

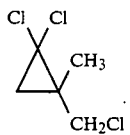

1,440 ml of a freshly prepared 50% strength sodium hydroxide solution are added dropwise to a mixture of 90.5 g (1 mole) of 3-chloro-2-methyl-1-propene, 1.5 liters of chloroform, 6 g of lithium bromide, 2.8 g of triethylbenzylammonium bromide and 24 ml of ethanol in the course of 2 hours, with vigorous stirring. During the dropwise addition, the temperature of the reaction vessel rises to 57° C. to 58° C. and is kept constant throughout the entire reaction time. When the addition has ended, the solution is stirred vigorously for a further hour and is then cooled to room temperature. After addition of 1 liter of chloroform and 1 liter of water, the organic phase is washed several times with water and then dried over magnesium sulphate. After the solvent has been removed under a waterpump vacuum and the residue has subsequently been rectified, 127 g (73% of theory) of 1-chloromethyl-2,2-dichloro-2-methyl-cyclopropane of refractive index $n_D^{20}$ 1.4860 are obtained.

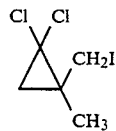

A mixture of 300 ml of acetone, 82.5 g (0.55 mole) of sodium iodide and 86.5 g (0.55 mole) of 1-chloromethyl-2,2-dichloro-2-methyl-cyclopropane is heated at 62° C. for 48 hours. After the mixture has been cooled to room temperature, the reaction product is concentrated under a waterpump vacuum at 50° C. The residue is taken up in 1 liter of methylene chloride and washed with 300 ml of water, 300 ml of dilute sodium thiosulphate solution and again with 300 ml of water. The organic phase is dried over magnesium sulphate and concentrated.

After distillation over a 20 cm Vigreux column, 121 g (83% of theory) of 1,1-dichloro-2-iodomethyl-2-methyl-cyclopropane of refractive index $n_D^{20}$: 1.5261 are obtained.

The remaining compounds of the formula (II) can be obtained in an analogous manner.

It is understood that the specification and examples are illustrative but not limitative of the present invention and that other embodiments within the spirit and scope of the invention will suggest themselves to those skilled in the art.

We claim:

1. A substituted cyclopropylmethyl(ene) ether of the formula

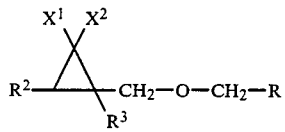

in which $X^1$ and $X^2$ are identical or different and represent halogen, $R^2$ represents hydrogen, methyl, halomethyl, alkinyloxymethyl or iodoalkinyloxymethyl, $R^3$ represents hydrogen or methyl, and R represents a triiodoalkenyl, alkinyl or iodoalkinyl radical.

2. A substituted cyclopropylmethyl(ene) ether according to claim 1, in which $X^1$ and $X^2$ are identical or different and represent fluorine, chlorine and/or bromine, $R^2$ represents hydrogen, methyl, halomethyl, $C_2$-$C_4$-alkinyloxymethyl or iodo-$C_2$-$C_4$-alkinyloxymethyl, and R represents triiodo-$C_2$-$C_4$-alkenyl, $C_2$-$C_4$-alkinyl or iodo-$C_2$-$C_4$-alkinyl.

3. A substituted cyclopropylmethyl(ene) ether according to claim 1, in which $X^1$ and $X^2$ are identical or different and represent chlorine and/or bromine, $R^2$ represents hydrogen, methyl, bromomethyl, propinyloxymethyl or iodopropinyloxymethyl, and R represents triiodoethenyl, ethinyl, iodoethinyl, propinyl or iodopropinyl.

4. A substituted cyclopropylmethyl ether according to claim 1, wherein such ether is 3-(2,2-dichloro-3-methylcyclopropylmethoxy)-1-propine of the formula

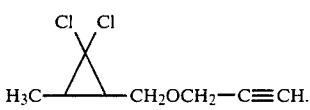

5. A substituted cyclopropylmethyl ether according to claim 1, wherein such ether is 3-(2,2-dichloro-1-methylcyclopropylmethoxy)-1-propine of the formula

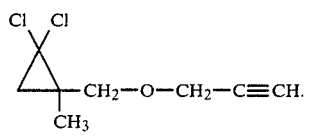

6. A substituted cyclopropylmethyl ether according to claim 1, wherein such ether is 3-(2,2-dibromo-cyclopropylmethoxy)-1-propine of the formula

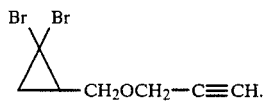

7. A substituted cyclopropylmethyl ether according to claim 1, wherein such ether is 3-(2,2-dibromo-3-methylcyclopropylmethoxy)-1-propine of the formula

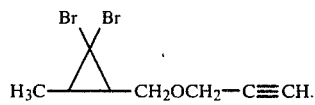

8. A substituted cyclopropylmethyl ether according to claim 1, wherein such ether is 3-(3-bromomethyl-2,2-dichloro-cyclopropylmethoxy)-1-propine of the formula

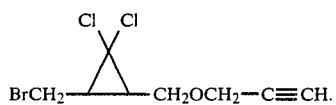

9. An arthropodicidal composition comprising an anthropodicidally effective amount of a compound according to claim 1 plus an additional ingredient.

10. A composition according to claim 9, wherein the additional ingredient comprises a known arthropodicide.

11. A composition according to claim 10, wherein the components are present in a weight ratio of about 1:5 to 5:1.

12. A composition according to claim 10, wherein the known arthropodicide is a carbamate.

13. A composition according to claim 10, wherein the known arthropodicide is a carboxylic acid ester.

14. A composition according to claim 10, wherein the known arthropodicide is a phosphoric or phosphonic acid ester.

15. A method of combatting arthropods which comprises administering to such arthropods or to a habitat thereof an arthropodicidally effective amount of a compound according to claim 1.

16. A method of combatting arthropods which comprises administering to such arthropods or to a habitat thereof an arthropodicidally effective amount of a composition according to claim 10.

17. The method according to claim 16, wherein the substituted cyclopropylmethyl ether is
3-(2,2-dichloro-3-methyl-cyclopropylmethoxy)-1-propine,
3-(2,2-dichloro-1-methyl-cyclopropylmethoxy)-1-propine,
3-(2,2-dibromo-cyclopropylmethoxy)-1-propine,
3-(2,2-dibromo-3-methyl-cyclopropylmethoxy)-1-propine or
3-(3-bromomethyl-2,2-dichloro-cyclopropyl-methoxy)-1-propine.

* * * * *

UNITED STATES PATENT AND TRADEMARK OFFICE
CERTIFICATE OF CORRECTION

PATENT NO. : 4,575,516
DATED : March 11, 1986
INVENTOR(S) : Bernd-Wieland Kruger, et al.

It is certified that error appears in the above-identified patent and that said Letters Patent is hereby corrected as shown below:

| | |
|---|---|
| Col. 1, line 19 | Insert -- - -- between "Springer" and "Verlag" |
| Col. 6, line 38 Table 1, line 9 under "$X^2$" | Delete "CL" and substitute --Cl-- |
| Col. 11, line 40 | Delete "ad" and substitute --and-- |
| Col. 12, line 18 | Correct spelling of --variant-- |
| Col. 12, line 33 | After "$X^2$," insert --$R^1$,-- |
| Col. 51, line 23 | Delete "$x^1$" and substitute --$X^1$-- |
| Col. 54, line 6 | Delete "represent" and substitute --represents-- |
| Col. 54, line 33 | After "methylthio" insert -- - -- |
| Col. 54, line 34 | After "propylideneamino" insert -- - -- |
| Col. 55, line 10 | Delete "chloride" and substitute --chlorine-- |
| Col. 55, line 45 | Middle structure, delete right side and substitute: 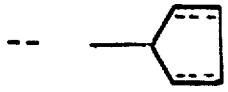 |
| Col. 55, line 45 | Third structure delete upper right side and substitute: 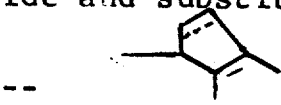 |
| Col. 55, line 62 | Delete "alkyl-lene-" and substitute --alkylene- -- |
| Col. 56, line 6 | Delete "(3,4)" and substitute |

UNITED STATES PATENT AND TRADEMARK OFFICE
CERTIFICATE OF CORRECTION

PATENT NO. : 4,575,516

DATED : March 11, 1986

INVENTOR(S) : Bernd-Wieland Kruger, et al.

It is certified that error appears in the above-identified patent and that said Letters Patent is hereby corrected as shown below:

| | |
|---|---|
| Col. 57, line 67 | --(3,4- -- Correct spelling of --Bruchidius-- |
| Col. 60, line 12 | After "against" delete "products," and insert --hygiene pests and pests of stored products, the active-- |
| Col. 60, line 4 under "Common name:" | Delete "(dioxocarb)" and substitute --(dioxacarb)-- |
| Col. 65, line 19 and Col. 66, line 5 | Before "%" delete "5" |
| Col. 66, line 58 | Delete right side of formula and substitute: -- $CH_2OCH_2C{\equiv}CH$ -- |

Signed and Sealed this

Fifteenth Day of July 1986

[SEAL]

Attest:

DONALD J. QUIGG

Attesting Officer

Commissioner of Patents and Trademarks